United States Patent [19]
Köster et al.

[11] Patent Number: 6,133,436
[45] Date of Patent: Oct. 17, 2000

[54] BEADS BOUND TO A SOLID SUPPORT AND TO NUCLEIC ACIDS

[75] Inventors: Hubert Köster, La Jolla, Calif.; David M. Lough, Berwickshire, United Kingdom

[73] Assignee: Sequenom, Inc., San Diego, Calif.

[21] Appl. No.: 08/933,792

[22] Filed: Sep. 19, 1997

Related U.S. Application Data

[63] Continuation-in-part of application No. 08/746,036, Nov. 6, 1996, Pat. No. 5,900,481.

[51] Int. Cl.[7] .......................... C07H 33/18; C07H 21/04; C07H 1/00
[52] U.S. Cl. ...................... 536/24.3; 536/25.3; 536/23.1; 525/332.2; 502/233
[58] Field of Search ................................ 536/25.3, 23.1, 536/24.3; 525/332.2; 502/233

[56] References Cited

U.S. PATENT DOCUMENTS

| | | | |
|---|---|---|---|
| 4,139,346 | 2/1979 | Rabbani | 422/56 |
| 4,582,789 | 4/1986 | Sheldon, III et al. | 435/6 |
| 4,683,194 | 7/1987 | Saiki et al. | 435/6 |
| 4,683,195 | 7/1987 | Mullis et al. | 435/6 |
| 4,725,677 | 2/1988 | Köster et al. | 536/27 |
| 4,729,947 | 3/1988 | Middendorf et al. | 435/6 |
| 4,749,742 | 6/1988 | Elmore | 525/54.11 |
| 4,757,141 | 7/1988 | Fung et al. | 536/27 |
| 4,794,150 | 12/1988 | Steel | 525/54.11 |
| 4,797,355 | 1/1989 | Stabinsky | 435/6 |
| 4,806,546 | 2/1989 | Carrico et al. | 536/27 |
| 4,855,225 | 8/1989 | Fung et al. | 435/6 |
| 4,882,127 | 11/1989 | Rosenthal et al. | 422/50 |
| 4,948,882 | 8/1990 | Ruth | 536/27 |
| 4,983,521 | 1/1991 | Lingappa et al. | 435/172.3 |
| 4,994,373 | 2/1991 | Stavrianopoulos et al. | 435/6 |
| 5,003,059 | 3/1991 | Brennan | 536/27 |

(List continued on next page.)

FOREIGN PATENT DOCUMENTS

| | | |
|---|---|---|
| 0360677 | 3/1990 | European Pat. Off. .......... C12Q 1/68 |
| 0396116 | 11/1990 | European Pat. Off. . |
| 0412883 | 2/1991 | European Pat. Off. . |
| 0455905 | 11/1991 | European Pat. Off. . |
| 0456304 | 11/1991 | European Pat. Off. . |
| 0684315 | 11/1995 | European Pat. Off. . |
| 0701001 | 3/1996 | European Pat. Off. . |
| 3930312 | 4/1990 | Germany . |
| 4011991 | 10/1990 | Germany . |
| 63-230086 | 9/1988 | Japan . |
| 2215399 | 8/1990 | Japan . |
| 6294796 | 10/1994 | Japan . |
| 2017105 | 3/1979 | United Kingdom . |
| 8402579 | 7/1984 | WIPO . |
| 8909282 | 10/1989 | WIPO . |
| 8909406 | 10/1989 | WIPO . |
| 8912624 | 11/1989 | WIPO . |
| 9001564 | 2/1990 | WIPO . |
| 9003382 | 4/1990 | WIPO . |
| 9007582 | 7/1990 | WIPO . |
| 9015883 | 12/1990 | WIPO . |
| 9106678 | 5/1991 | WIPO . |
| 9113075 | 9/1991 | WIPO . |
| 9203575 | 3/1992 | WIPO . |
| 9207879 | 5/1992 | WIPO . |
| 9210092 | 6/1992 | WIPO . |
| 9213629 | 8/1992 | WIPO . |
| 9215712 | 9/1992 | WIPO . |
| 9306925 | 4/1993 | WIPO . |
| 9309668 | 5/1993 | WIPO . |
| 9320236 | 10/1993 | WIPO . |
| 9411529 | 5/1994 | WIPO . |
| 9411530 | 5/1994 | WIPO . |
| 9411735 | 5/1994 | WIPO . |
| 9416101 | 7/1994 | WIPO . |
| 9421822 | 9/1994 | WIPO . |
| 9504524 | 2/1995 | WIPO . |
| 9530773 | 11/1995 | WIPO . |
| 9531429 | 11/1995 | WIPO . |
| 9637630 | 5/1996 | WIPO . |
| 9619587 | 6/1996 | WIPO ............................ C12Q 1/68 |
| 9629431 | 9/1996 | WIPO . |
| 9632504 | 10/1996 | WIPO . |
| 9636731 | 11/1996 | WIPO . |
| 9636732 | 11/1996 | WIPO . |
| 9708306 | 3/1997 | WIPO . |
| 9716699 | 5/1997 | WIPO . |
| 9733000 | 9/1997 | WIPO . |
| 9737041 | 10/1997 | WIPO . |
| 9742348 | 11/1997 | WIPO . |
| 9743617 | 11/1997 | WIPO . |
| 9812355 | 3/1998 | WIPO . |
| 9820019 | 5/1998 | WIPO . |
| 9820020 | 5/1998 | WIPO . |
| 9820166 | 5/1998 | WIPO . |
| 9854751 | 12/1998 | WIPO . |

OTHER PUBLICATIONS

Alderton et al., Magnetic bead purification of M13 DNA sequencing templates, *Anal. Biochem.* 201:166–169 (1992).

Allin, S.M.and Shuttleworth, S.J., "The Preparation and First Application of a Polymer–Supported "Evans" Oxazolidinone", *Tetrahedron Lett.*, 37(44):8023–8026 (1996).

Arlinghaus et al., Applications of resonance ionization spectroscopy for semiconductor, environmental and biomedical analysis, and for DNA sequencing, *SPIE*, vol. 1435, *Opt. Methods Ultrasensitive Detect. Anal. Tech. Appl.* pp. 26–35 (1991).

(List continued on next page.)

*Primary Examiner*—Gary L. Kunz
*Attorney, Agent, or Firm*—Stephanie L. Seidman; Heller Ehrman White & McAuliffe LLP

[57] ABSTRACT

Novel compositions comprised of at least one bead conjugated to a solid support and further conjugated to at least one nucleic acid and preferred methods for making the novel compositions are described. As compared to "flat" surfaces, beads linked to a solid support provide an increased surface area for immobilization of nucleic acids. Furthermore, by selecting a bead with the desired functionality, a practitioner can select a functionalization chemistry for immobilizing nucleic acids, which is different from the chemistry of the solid support.

23 Claims, 14 Drawing Sheets

U.S. PATENT DOCUMENTS

| | | | |
|---|---|---|---|
| 5,037,882 | 8/1991 | Steel | 525/54.11 |
| 5,045,694 | 9/1991 | Beavis et al. | 250/287 |
| 5,064,754 | 11/1991 | Mills | 435/6 |
| 5,077,210 | 12/1991 | Eigler et al. | 435/176 |
| 5,082,935 | 1/1992 | Cruickshank | 536/27 |
| 5,118,605 | 6/1992 | Urdea | 435/6 |
| 5,118,937 | 6/1992 | Hillenkamp et al. | 250/282 |
| 5,135,870 | 8/1992 | Williams et al. | 436/86 |
| 5,149,625 | 9/1992 | Church et al. | 435/6 |
| 5,198,531 | 3/1993 | Webber et al. | 525/332.2 |
| 5,210,412 | 5/1993 | Levis et al. | 250/288 |
| 5,221,518 | 6/1993 | Mills | 422/62 |
| 5,234,824 | 8/1993 | Mullis | 435/91 |
| 5,237,016 | 8/1993 | Ghosh et al. | 525/329.4 |
| 5,242,974 | 9/1993 | Holmes | 525/54.11 |
| 5,283,342 | 2/1994 | Gustavson et al. | 548/304.1 |
| 5,288,644 | 2/1994 | Beavis et al. | 436/94 |
| 5,380,833 | 1/1995 | Urdea | 536/22.1 |
| 5,410,068 | 4/1995 | Coull et al. | 548/545 |
| 5,430,136 | 7/1995 | Urdea et al. | 536/243 |
| 5,436,327 | 7/1995 | Southern et al. | 536/25.34 |
| 5,474,895 | 12/1995 | Ishii et al. | 435/6 |
| 5,478,893 | 12/1995 | Ghosh et al. | 525/329.4 |
| 5,484,701 | 1/1996 | Cocuzza et al. | 435/6 |
| 5,492,821 | 2/1996 | Callstrom et al. | 435/188 |
| 5,503,980 | 4/1996 | Cantor | 435/6 |
| 5,506,348 | 4/1996 | Pieles | 536/23.1 |
| 5,512,439 | 4/1996 | Hornes et al. | 435/6 |
| 5,514,548 | 5/1996 | Krebber et al. | 435/6 |
| 5,527,675 | 6/1996 | Coull et al. | 435/6 |
| 5,541,313 | 7/1996 | Ruth | 536/24.3 |
| 5,545,539 | 8/1996 | Miller | 435/91.2 |
| 5,547,835 | 8/1996 | Köster et al. | 435/6 |
| 5,552,535 | 9/1996 | McLean et al. | 536/23.1 |
| 5,571,902 | 11/1996 | Ravikumar et al. | 536/22.1 |
| 5,580,733 | 12/1996 | Levis et al. | 435/6 |
| 5,583,042 | 12/1996 | Roth | 435/288.1 |
| 5,601,982 | 2/1997 | Sargent et al. | 435/6 |
| 5,605,798 | 2/1997 | Köster | 435/6 |
| 5,612,474 | 3/1997 | Patel | 536/27.14 |
| 5,616,698 | 4/1997 | Krepinsky et al. | 536/18.6 |
| 5,616,700 | 4/1997 | Reddy et al. | 536/25.3 |
| 5,622,824 | 4/1997 | Köster | 435/6 |
| 5,624,711 | 4/1997 | Sundberg et al. | 427/261 |
| 5,631,134 | 5/1997 | Cantor | 435/6 |
| 5,635,598 | 6/1997 | Lebl et al. | 530/334 |
| 5,639,633 | 6/1997 | Callstrom et al. | 435/68.1 |
| 5,641,862 | 6/1997 | Rutter et al. | 530/334 |
| 5,643,722 | 7/1997 | Rothschild et al. | 435/6 |
| 5,643,798 | 7/1997 | Beavis et al. | 436/94 |
| 5,648,462 | 7/1997 | Funakoshi et al. | 530/344 |
| 5,648,480 | 7/1997 | Letsinger et al. | 536/25.34 |
| 5,652,358 | 7/1997 | Pfleiderer et al. | 536/25.3 |
| 5,663,242 | 9/1997 | Ghosh et al. | 525/329.4 |
| 5,668,266 | 9/1997 | Ruth | 536/25.3 |
| 5,670,322 | 9/1997 | Eggers et al. | 435/6 |
| 5,677,195 | 10/1997 | Winkler et al. | 436/518 |
| 5,679,773 | 10/1997 | Holmes | 530/334 |
| 5,691,141 | 11/1997 | Köster | 435/6 |
| 5,700,642 | 12/1997 | Monforte et al. | 435/6 |
| 5,726,243 | 3/1998 | Fields | 525/54.11 |
| 5,736,625 | 4/1998 | Callstrom et al. | 530/402 |
| 5,736,626 | 4/1998 | Mullah et al. | 536/25.3 |
| 5,742,049 | 4/1998 | Holle et al. | 250/282 |
| 5,795,714 | 8/1998 | Cantor et al. | 435/6 |
| 5,830,655 | 11/1998 | Monforte et al. | 435/6 |
| 5,864,137 | 1/1999 | Becker et al. | 250/287 |
| 5,869,242 | 2/1999 | Kamb | 435/6 |

OTHER PUBLICATIONS

Arshady, Reza, Beaded polymer supports and gels: I. Manufacturing techniques, *Journal of Chromatography*, 586:181–197 (1991).

Arshady, Reza, Beaded polymer supports and gels: II. Physico–chemical criteria and functionalization, *Journal of Chromatography*, 586:199–219 (1991).

Backes, B.J. et al., "Activation Method to Prepare a Highly Reactive Acylsulfonamide "Safety Catch" Linker for Solid–Phase Synthesis[1]", *J. Am. Chem. Soc.*, 118:3055–3056 (1996).

Bains, DNA sequencing by mass spectrometry: Outline of a potential future application, *Chimicaoggi* 9:13–16 (1991).

Bains, Setting a sequence to sequence a sequence, *Biotechnology* 10:757–758 (1992).

Bannwarth, Solid–phase synthesis of oligodeoxynucleotides containing phosphoramidate internucleotide linkages and their specific chemical cleavage, *Helvctica Chimica Acta* 71:1517–1527 (1988).

Barrell, DNA sequencing: present limitations and prospects for the future, *FASEB J. 5:* 40–45 (1991).

Batista–Viera et al., A new method for reversible immobilization of thiol biomolecules bsed on solid–phase bound thiolsulfonate groups, *App. Biochem and Biotech*, 31:175–195 (1991).

Beaucage et al., The synthesis of modified oligonucleotides by the phosphoramidite approach and their applications, *Tetrahedron 49*:6123–6194 (1993).

Beck and Köster, Applications of dioxetane chemiluminescent probes to molecular biology, *Anal. Chem.* 62:2258–2270 (1990).

Beck et al., Chemiluminescent detection of DNA: application of DNA sequencing and hybridization, *Nucleic Acids Res. 17*(13):5115–5123 (1989).

Bray, A.M. et al., "Direct Cleavage of Peptides from a Solid Support into Aqueous Buffer. Application in Simultaneous Multiple Peptide Synthesis", *J. Org. Chem.*, 56:6659–6666 (1991).

Brennan et al., New methods to sequence DNA by mass spectrometry, *SPIE*, vol. 1206, *New Technol. Cytom. Mol. Biol.* pp. 60–77 (1990).

Broude et al., Enhanced DNA sequencing by hybridization, *Proc. Natl. Acad. Sci. 91*:3072–3076 (1994).

Brown et al., A single–bead decode strategy using electrospray ionization mass spectrometry and a new photolabile linker: 3–Amino–3–(2–nitrophenyl)propionic acid, *Molec. Diversity 1*:4–12 (1995).

Burgess, K. et al., "An Approach to Photolabile, Fluorescent Protecting Groups", *J. Org. Chem.*, 62:5165–5168 (1997).

Chen and Seeburg, Supercoil sequencing: A fast and simple method for sequencing plasmid DNA, *DNA 4*(2):165–170 (1985).

Chrisey et al., Covalent attachment of synthetic DNA to self–assembled monlayer films, *Nucl. Acids Res.* 24:3031–3039 (1996).

Chrisey et al., Fabrication of patterned DNA surfaces, *Nucl. Acids. Res.* 24:3040–3047 (1996).

Church et al., "Multiplex DNA Sequencing", *Science* 240:185–188 (1988).

Crain, "Mass spectrometric techniques in nucleic acid research", *Mass Spectr. Rev. 9*:505–554 (1990).

Damha, Masad J. et al.; An Improved Procedure for Derivatization of Controlled–Pore Glass Beads for Solid–Phase Oligonucleotide Synthesis, *Nucleic Acids Research* 18(13):3813–3821 (1990).

Derwent Publications, WPI Acc. No. #85–224987/198942, citing International PCT Application No. WO 89/09406 published Oct. 05, 1989.

Derwent Publications, WPI Acc. No. #88–311964/198844, citing Japanese Patent No. JP 63230086 published Sep. 26, 1988.

Derwent Publications, WPI Acc. No. #90–108917/199015, citing European Patent No. EP 0360677 published Mar. 28, 1990.

Derwent Publications, WPI Acc. No. #90–133198/199018, citing German Patent No. DE 3930312 published Apr. 26, 1990.

Derwent Publications, WPI Acc. No. #90–321790/199043, citing German Patent No. DE 4011991 published Oct. 18, 1990.

Derwent Publications, WPI Acc. No. #90–302767/199040, citing Japanese Patent No. JP 2215399 published Aug. 28, 1990.

DeGrado, W.F. and Kaiser, E.T., "Polymer–Bound Oxime Esters as Supports for Solid–Phase Peptide Synthesis. Preparation of Protected Peptide Fragments", *J. Org. Chem.*, 45:1295–1300 (1980).

Drmanac, et al., Sequencing of megabase plus DNA by hybridization: Theory of the method, *Genomics* 4:114–128 (1989).

Eckstein, Nucleoside phosphorothioates, *Ann. Rev. Biochem.* 54:367–402 (1985).

Eckstein and Goody, Synthesis and properties of diastereoisomers of adenosine 5'–(O–1–thiotriphosphate) and adenosine 5'–(O–2–thiotriphosphate), *Biochemistry* 15(8):1685–1691 (1976).

Eckstein, F., Phosphorothioate analogues of nucleotides, *Accounts Chem. Res.* 12:204–210 (1979).

Frank and Köster, DNA chain length and the influence of base composition on electrophoretic mobility of oligodeoxyribonucleotides in polyacrylamide–gels, *Nucl. Acids. Res.* 6:2069–2087 (1979).

Fu et al., "A DNA sequencing strategy that requires only five bases of known terminal sequencing for priming", *Proc. Natl. Acad. Sci.* 92:10162–10166 (1995).

Fujita et al., Surprising lability of biotin–streptavidin bond during transcription of biotinylated DNA bound to paramagnetic beads, *BioTechniques* 14:608–617 (1993).

Gait, M.J., ed., "Oligonucleotide Synthesis : A Practical Approach", IRL Practical Approach Series, IRL Press, Oxford, 1984.

Gayo, L.M. and Suto, M.J., "Traceless Linker: Oxidative Activation and Displacement of a Sulfur–Based Linker", *Tetrahedron Lett.*, 38(2):211–214 (1997).

Ghosh and Musso, Covalent attachment to solid supports, *Nucl. Acids Res.* 15:5353–5372 (1987).

Gildea et al., A versatile acid–labile linker for modification of synthetic biomolecules, *Tetrahedron Letters* 31:7095–7398 (1990).

Goldmacher et al., Photoactivation of toxin conjugates, *Bioconjugate Chem.* 3:104–107, (1992).

Greene, *Protective Groups in Organic Synthesis*, 2nd Edition, Wiley & Sons, Table of Contents (1991).

Han, Y. et al., "Silicon Directed ipso–Substitution of Polymer Bound Arylsilanes: Preparation of Biaryls via the Suzuki Cross–Coupling Reaction", *Tetrahedron Lett.*, 37(16):2703–2706 (1996).

Hayashi et al., Immobilization of thiol proteases onto porous poly(vinyl alcohol) beads, *Polymer Journal*, 25:5, 489–497 (1993).

Hazum et al., A photocleavable protecting group for the thiol function of cysteine, *Pept., Proc. Eur. Pept. Symp., 16th*, Brunfeldt, K (Ed), pp. 105–110 (1981).

Hermanson, *Bioconjugate Techniques*, Academic Press (1996).

Higuchi et al., A general method of in vitro preparation and mutagenesis of DNA fragments: Study of protein and DNA interactions, *Nucleic Acids Res.* 16:7351–7367 (1988).

Higuchi et al., Kinetic PCR analysis: Real–time monitoring of DNA amplification reactions, *Bio/Technology* 11:1026–1030 (1993).

Hillenkamp et al., "Matrix Assisted UV_Laser Desorption/ionization: A New Approach to Mass Spectrometry of Large Biomolecules", *Bio Mass Spectr.*, Burlingame and McCloskey (eds.), pp. 49–61, Elsevier Science Publishers B.V., Amsterdman (1989).

Hillenkamp and Ehring, Laser desorption mass spectrometry Part 1: Basic mechanisms and techniques, *Mass Spectrometry in the Biological Sciences: A tutorial*, pp. 165–179 (1992).

Hobbs and Eckstein, A general method for the synthesis of 2'–azido–2'deoxy–and 2'–amino–2'–deoxyribofuranoxyl purines, *J. Org. Chem.* 42:714–719 (1976).

Hornes and Korsnes, Magnetic DNA hybridization of oligonucleotide probes attached to superparamagnetic beads and their use in the isolation of Poly(A) mRNA from eukaryotic cells, *GATA* 7:145–150, (1990).

Hultman et al., Direct solid phase sequencing of genomic and plasmid DNA using magnetic beads as solid support, *Nucl. Acids Res.* 17:4937–4946 (1989).

Huth–Fehre et al., Matrix–assisted laser desorption mass spectrometry of oligodeoxythymidulic acids, *Rapid Communications in Mass Spectrometry* 6(3):209–213 (1992).

Hyman, A new method of sequencing DNA, *Anal. Biochem.* 174:423–436 (1988).

Innis et al., DNA sequencing with *Thermus aquaticus* DNA polymerase and direct sequencing of polymerase chain reaction–amplified DNA, *Proc. Natl. Acad. Sci. USA* 85:9436–9440 (1988).

Innis et al., editors, *PCR Protocols: A quide to methods and applications*, Academic Press, San Diego (1990).

Jacobson, et al. Applications of mass spectrometry to DNA sequencing, *GATA* 8:223–229 (1991).

Jett et al., "High–Speed DNA Sequencing: An Approach Based Upon fluorescence Detection of Single Molecules", *J. Bio Strut & Dynam.* 7(2):301–09 (1989).

Jurinke, C. et al., "Recovery of Nucleic Acids from Immobilized Biotin–Streptavidin Complexes using Ammonium Hydroxide and Applications in MALDI–TOF Mass Spectrometry", *Anal. Chem.*, 69:904–910 (1997).

Kaldor, S.W. et al., "Use of Solid Supported Nucleophiles and Electrophiles for the Purification of Non–Peptide Small Molecule Libraries", *Tetrahedron Lett.*, 37(40):7193–7196 (1996).

Khrapko et al., An oligonucleotide hybridization approach to DNA sequencing, *FEB* 256(1,2):118–122 (1989).

Khrapko et al., "A method for DNA sequencing by hybridization with oligonucleotide matrix", *J. DNA Sequencing and Mapping* 1:375–388 (1991).

Kirpekar et al., "7–deaza purine bases offer a higher ion stability in the analysis of DNA by matrix–assisted laser desorption/ionization mass spectrometry" *Rapid Commun. Mass Spectrom.* 9:525–531 (1995).

Koster, H. et al., "Polymer Support Oligonucleotide Synthesis—XV: Synthesis of Oligodeoxynucleotides on Controlled Pore Glass (CPG) using Phosphate and a new Phosphotriester Approach", *Tetrahedron*, 40(1):103–112 (1984).

Koster, H. et al., "Some Improvements in the Synthesis of DNA of Biological Interest", *Nucl. Acids Res.*, Symposium Ser. 7:39–59 (1980).

Köster et al., "A stragegy for rapid and efficient DNA sequencing by mass spectrometry", *Nature Bio* 14:1123–1128 (1996).

Köster et al., N–acyl protecting groups for deoxynucleotides: A quantitative and comparative study, *Tetrahedron* 37:363–369 (1981).

Köster et al., Well–defined insoluble primers for the enzymatic synthesis of oligo– and polynucleotides, *Hoppe Seylers Z. Physiol. Chem.* 359(11):1579–1589 (1978).

Köster et al., Oligonucleotide synthesis and multiplex DNA sequencing using chemiluminescent detection, *Nucl. Acids Res., Symposium Series No.* 24:318–321, (1991).

Kozal et al., "Extensive polymorphisms observed in HIV–1 clade B protease gene using high–density oligonucleotide arrays", *Nature Medicine* 2(7):753–759 (1996).

Kumar, G. and Poonian, M.S., "Improvements in Oligodeoxyribonucleotide Synthesis: Methyl N,N–Dialkylphosphoramidite Dimer Units for Solid Support Phosphite Methodology", *J. Org. Chem.*, 49:4905–4912 (1984).

Kussmann, et al., Matrix–assisted laser desorption/ionization mass spectrometry sample preparation techniques designed for various peptide and protein analytes, *J. Mass Spec.* 32:593–601 (1997).

Labeit et al., Laboratory methods: A new method of DNA sequencing using deoxynucleoside α–thiotriphophates, *DNA* 5:173–177 (1986).

Lamture et al., Direct detection of nucleic acid hybridization on the surface of a charge coupled device, *Nucl. Acids Res.* 22:2121–2125 (1994).

Landegren et al., "DNA Diagnostics—Molecular techniques and automation", *Science* 242:229–237 (1988).

Leznoff, C.C. and Wong, J.Y., "The Use of Polymer Supports in Organic Synthesis. The Synthesis of Monotrityl Ethers of Symmetrical Diols" *Can. J. Chem.*, 50:2892–2893 (1972).

Li et al., "Analysis of single mammalian cell lysates by mass spectrometry", *J. Am. Chem. Soc.* 118:11662–11663 (1996).

Li et al., "High–Resolution MALDI Fourier Transform Mass Spectrometry of Oligonucleotides", *Anal Chem* 68(13):2090–2096 (1996).

Little et al., "Direct detection of synthetic and biologically generated double–stranded DNA by MALDI–TOF MS", *J. Mass Spec* 17:1–8 (1997).

Little et al., "Mass spectrometry from miniaturized arrays for full comparative DNA analysis", *Nature Med* 3(12):1413–1416 (1997).

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet", *Anal chem* 69:4540–4546 (1997).

Lloyd–Williams, P. et al., "Convergent Solid–Phase Peptide Synthesis", *Tetrahedron*, 49(48):11065–11133 (1993).

Lorsbach, B.A. et al., "Reissert–Based "Traceless" Solid–Phase Synthesis: Isoquinoline, and Isoxazoline–Containing Heterocycles", *J. Org. Chem.*, 61:8716–8717 (1996).

Lund et al., Assessment of methods for covalent binding of nucleic acids to magnetic beads, Dynabeads™ and the characteristics of the bound nucleic acids in hybridization reactions, *Nucl. Acids Res.* 16:10861–10880 (1988).

Manoharan et al., A 2'–O–thiol tether in the ribose moiety of nucleic acids for conjugation chemistry, *Gene*, 149:147–156 (1994).

Matteucci et al., Synthesis of deoxyoligonucleotides on a polymer support, *J. A. Chem. Soc.* 103:3185–3191, 1981.

Maxam and Gilbert, Sequencing end–labeled DNA with base–specific chemical cleavages, *Methods in Enzymology* 65:499–560 (1980).

McCray and Trentham, "Properties and uses of photoreactive caged compounds", *Annu. Rev. Biophys. Biophys. Chem.* 18:239–270 (1989).

*Molecular Cloning: A laboratory manual*, 2nd, ed., Ch. 11: Synthetic oligonucleotide probes, Sambrook, Cold Spring Harbor Laboratory Press New York, pp. 11.1–11.61 (1989).

Morphy, J.R. et al., "A Novel Linker Strategy for Solid–Phase Synthesis", *Tetrahedron Lett.*, 37(18):3209–3212 (1996).

Murray, "DNA sequencing by mass spectrometry", *J. Mass. Spect.* 31:1203–1215 (1996).

Nakamaye et al., "Direct sequencing of polymerase chain reaction amplified DNA fragments through the incorporation of deoxynucleoside α–thiotriphosphates", *Nucleic Acids Res.* 16(21):9947–9959 (1988).

Nelson et al., "Volatilization of High Molecular Weight DNA by Pulsed Laser Ablation of Frozen Aqueous Solutions", *Science* 246:1585–1587 (1989).

Nelson et al., Time–of–flight mass spectrometry of nucleic acids by laser ablation and ionization from a frozen aqueous matrix, *Rapid Communications in Mass Spectrometry* 4:348–351 (1990).

Newlander, K.A. et al., "Simple Silyl Linker for the Solid Phase Organic Synthesis of Aryl–Containing Molecules", *J. Org. Chem.*, 62:6726–6732 (1997).

Newton et al., The production of PCR products with 5' single–stranded tails using primers that incorporate novel phosphoramidite intermediates, *Nucl. Acids. Res.* 21:1155–1162 (1993).

Nikiforov and Rogers, The use of 96–well polystyrene plates for DNA hybridization–based assays: An evaluation of different approaches to oligonucleotide immobilization, *Anal. Biochem.* 227:201–209 (1995).

Nordhoff et al., "Ion stability of nucleic acids in infrared matrix–assisted laser desorption/ionization mass spectrometry", *Nuc Acids Res.* 21(15):3347–3357 (1993).

Nordoff et al., "Matrix–assisted laser desorption/ionization mass spectrometry of nucleic acids with wavelength in the ultraviolet and infrared", *Rapid Comm. Mass Spectrom.* 6:771–776 (1992).

Norton, J.C. et al., "Targeting Peptide Nucleic Acid–Protein Conjugates to Structural Features within Duplex DNA", *Bioorg. Med. Chem.*, 3(4):437–445 (1995).

O'Donnell et al., "MassArray as an Enabling Technology for the Industrial–Scale Analysis of DNA", *Genetic Engineering News* 17(21) (1997).

O'Donnell et al., "High–Density, Covalent Attachment of DNA to Silicon Wafers for Analysis by MALDI–TOF Mass Spectrometry", *Analytical Chemistry* 69(13):2438–2443 (1997).

O'Donnell–Maloney et al., "Microfabrication and array technologies for DNA sequencing and diagnostics", *Genetic Analysis: Biomolecular Engineering* 13:151–157 (1996).

Olejnik, J. et al., "Photocleavable biotin phosphoramidite for 5'–end–labelling, affinity purification and phosphorylation of synthetic oligonucleotides", *Nucl. Acids Res.*, 24(2):361–366 (1996).

*Oligonucleotides and Analogues, A Practical Approach*, F. Eckstein, editor, IRL Press Oxford, Table of Contents (1991).

*Oligonucleotides and Analogues: A Practical Approach*, Eckstein, edr., Oxford University Press Ch. 3, pp. 49–59, 137–139, 255–259 (1991).

Overberg et al., "Laser Desorption Mass Spectrometry. Part II Performance and Applications of Matrix–Assisted Laser Desorption/Ionization of Large Biomolecules", *Mass Spect in the Biolog Science: A Tutorial* 181–197 (1992).

Patek, M. and Lebl, M., "Safety–Catch Anchoring Linkage for Synthesis of Peptide Amides by Boc / Fmoc Strategy", *Tetrahedron Lett.*, 32(31):3891–3894 (1991).

Pieles et al., Matrix–assisted laser desorption ionization time–of–flight mass spectrometry: a powerful tool for the mass and sequence analysis of natural and modified oligonucleotides, *Nucleic Acids Res.* 21(14):3191–3196 (1993).

Pierce ImmunoTechnology Catalog, p. 57 (1993).

Pierce Catalog, pp. T123–T154, 1994.

Plunkett, M.J. and Ellman, J.A., "A Silicon–Based Linker for Traceless Solid–Phase Synthesis", *J. Org. Chem.*, 60:6006–6007 (1995).

Pon, et al., Derivation of controlled pore glass beads fo rsolid phase oligonucleotide synthesis, *BioTechniques*, 6:8, 770–775 (1988).

Raftery, et al., Characterization of a mutant recombinant S100 protein using electrospray ionization mass spectrometry. *Rapid Comm. Mass Spec.* 11:405–409 (1997).

Rasmussen et al., Covalent immobilization of DNA onto polystyrene microwells: The molecules are only bound at the 5'end, *Anal. Biochem.* 198:138–142 (1991).

Rink, "Solid–phase synthesis of protected peptide fragments using a trialkoxy–diphenyl–methlester resin", *Tetrahedron Lett.* 28:3787–3790 (1987).

Rolfs et al., *PCR: Clinical Diagnostics and Research*, Spring– Verlag (1992).

Routledge, A. et al., "The Use of a Dithiane Protected Benzoin Photolabile Safety Catch Linker for Solid Phase Synthesis", *Tetrahedron Lett.*, 38(7):1227–1230 (1997).

Running and Urdea, A procedure for productive coupling of synthetic oligonucleotides to polystyrene microtiter wells for hybridization capture, *Biotechniques* 8:276–277 (1990).

Ruppert et al., "Preparation of plasmid DNA as Sequencing Templates in a Microtiter Plate Format", Paper presented, Cold Spring Harbor Laboratory.

Ruppert et al., "A rapid and high throughput method for plasmid isolations", Presented: Automation in Mapping and DNA Sequencing Conference, Aug. 31–Sep. 2, 1994.

Saiki et al., Genetic analysis of amplified DNA with immobilized sequence–specific oligonucleotide probes, *Proc. Natl. Acad. Sci.* 86:6230–6234 (1989).

Salmon, S.E. et al., "Discovery of Biologically Active Peptides in Random Libraries: Solution Phase Testing after Staged Orthogonal Release from Resin Beads", *Proc. Natl. Acad. Sci. USA*, 90:11708–11712 (1993).

Sanger et al., DNA sequencing with chain–terminating inhibitors, *Proc. Natl. Acad. Sci.* 74:5463–67 (1977).

Sasaki et al., Introduction of an azide group into some uridine derivatives via 2',3'–benzoxonium and 2',3'–azidonium intermediates, *J. Org. Chem.* 41:3138–3143 (1976).

Schneider and Chait, Increased stability of nucleic acids containing 7–deaza–guanosine and 7–deaza–adenosine may enable rapid DNA sequencing by matrix–assisted laser desorption mass spectrometry, *Nucleic Acids Res.* 23(9):1570–1575 (1995).

Schram, Karl H., "Mass Spectrometry of Nucleic Acid Components", *Bio Appl of Mass Spect.* 34:203–287 (1990).

Senter et al., Novel photocleavable protein crosslinking reagents and their use in the preparation of antibody–toxin conjugates, Photochem. Photobiol. 42:231–237, (1985).

Sequenom Uses DNA MassArray™to Sequence Section of Human Cancer–Related p53 Gene, Press Release: Mar. 27, 1998, http://www.sequenom.com/pressrelease.htm.

Sequenom Signs Agreement With Bruker–Franzen Analytik to Develop Mass Spectrometer for DNA Massarray Analysis, Press Release: Jan. 12, 1998, http://www.sequenom.com/pressrelease.htm.

Sequenom Advances the Indusrial Genomics Revolution with the Launch of Its DNA MassArray™Automated Process Line, Press Release: Sep. 28, 1998, http://www.sequenom.com/pressrelease.htm.

Sequenom Reports DNA MassArray™Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

Sequenom Reports On Use of Its DNA MassArray™Technology to Analyze Genes Associated with Alzheimer's Disease adn Arteriosclerosis: Technology Has Applications in Drug Development, Press Release: Sep. 22, 1997. http://www.sequenom.com/pressrelease.htm.

Shaler et al., "Analysis of enzymatic DNA sequencing reactions by matrix–assisted laser desorption/ionization time–of–flight mass spectrometry", *Rapid Commun Mass Spectrom* 9(10):942–947 (1995).

Shaler et al., "Effect of Impurities on the matrix–Assisted Laser Desorption Mass Spectra of Single–Stranded Oligodeoxynucleotides", *Anal. Chem.* 68:576–579 (1996).

Siegert et al., "Matrix–assisted laser desorption/ionization time–of–flight mass spectrometry for the detection of polymerase chain reaction products containing 7–deazapurine moieties", *Analytical Biochemistry* 243:55–65 (1996).

Singh et al., Oligonucleotides, part 5 + : synthesis and fluorescence studies of DNA oligomers $d(AT)_5$ containing adenines covalently linked at C–8 with dansyl fluorophore, *Nucleic Acids Res.* 18(11):3339–3345 (1990).

Sinha et al., β–cyanoethyl N,N–dialkylamino/N–morpholinomonochloro phosphoamidites, new phosphitylating agents facilitating ease of deprotection and work–up of synthesized oligonucleotides, *Tetrahedron Lett.* 24:5843–5846 (1983).

Sinha et al., Polymer support oligonucleotide synthesis XVIII: use of β–cyanoethyl–N,N–dialkylamino–/N–morpholino phosphoramidite of deoxynucleosides for the synthesis of DNA fragments simplyfying deprotection and isolation of the final product, *Nucleic Acids Res.* 12:4539–4557 (1984).

Slim et al., Configurationally defined phosphorothioate–containing oligoribonucleotides in the study of the mechanism of cleavage of hammerhead ribozymes, *Nucleic Acids Res.* 19:1183–1188 (1991).

Sproat et al., The synthesis of protected 5'–amino–2', 5'–dideoxyribonucleoside–3'–O–phosphoramidites; applications of 5'–amino–oligodeoxyribonucleotides, *Nucleic Acids Res.* 15:6181–6196 (1987).

Sproat et al., The synthesis of protected 5'–mercapto–2', 5'–dideoxyribonucleoside–3'–O–phosphoramidites; uses of 5'mercapto–oligodeoxyribonucleotides, *Nucleic Acids Res.* 15:4837–4848 (1987).

Stahl et al., Solid Phase DNA Sequencing using the Biotin–Avidin System, *Nucleic Acids Research*, vol. 16, No. 7, pp. 3025–3039 (1988).

Strezoska et al., DNA sequencing by hybridization: 100 bases read by a non–gel–based method, *Proc. Natl. Acad. Sci.* 88:10089–10093 (1991).

Tang et al., "Matrix–assisted laser desorption/ionization mass spectrometry of immobilized duplex DNA probes", *Nucleic Acids Research* 23:3126–3131 (1995).

Tang et al., Detection of 500–nucleotide DNA by laser desorption mass spectrometry, *Rapid Commun. Mass Spectrom.* 8:727–730 (1994).

Thuong and Asseline, Oligonucleotides attached to intercalators, photoreactive and cleavage agents, *Oligonucleotides and Analogues: A Practical Approach*, Eckstein, edr., Oxford University Press Ch. 12, pp. 283–308 (1991).

Tong et al., Solid–phase method for the purification of DNA sequencing reactions, *Anal. Chem.* 64:2672–2677, (1992).

van Maarseveen, J.H. et al., "Solid Phase Ring–Closing Metathesis: Cyclization / Cleavage Approach towards a Seven Membered Cycloolefin", *Tetrahedron Lett.*, 37(45):8249–8252 (1996).

Vorm, et al., Improved resolution and very high sensitivity in MALDI TOF of matrix surfaces made by fast evaporation, *Anal. Chem.* 66:3281–3287 (1994).

Wang, Solid phase synthesis of protected peptides via photolytic cleavage of the α–methylphenacyl ester anchoring linkage, *J. Org. Chem.* 41(20):3258–3261 (1976).

Wellhöner et al., Uptake and concentration of bioactive macromolecules by K562 cells via the transferrin cycle utilizing an acid–labile transferrin conjugate, *J. Biol. Chem.* 256:4309–4314, (1991).

Wentrup, *Reactive Molecules*, John Wiley & Sons, Table of Contents (1984).

Williams, Time of flight mass spectrometry of DNA laser–ablated from frozen aqueous solutions: applications to the Human Genome Project, Intl. J. Mass Spectrom. and Ion Processes 131:335–344 (1994).

Wolter et al., Negative Ion FAB mass spectrometric analysis of non–charged key intermediates in oligonucleotide synthesis: Rapid indentification of partially protected dinucleoside monophosphates, *Biomedical Environmental Mass Spectrometry* 14:111–116 (1987).

Wong, Conjugation of proteins to solid matrices, *Chemistry of Protein Conjugation and Cross–Linking*, Table of Contents (1993).

Wong, Conjugation of proteins to solid matrices, *Chemistry of Protein Conjugation and Cross–Linking* 12:295–317 (1993).

Wu et al., "Matrix–assisted Laser Desorption Time–of–flight Mass Spectrometry of Oligonucleotides Using 3–Hydroxypicolinic Acid as an Ultraviolet–sensitive Matrix", *Rapid Comm Mass Spec* 7:142–146 (1993).

Wu et al., "Time–of–Flight Mass Spectrometry of Underivatized Single–Stranded DNA Oligomers by Matrix–Assisted Laser Desorption", *Anal. Chem.* 66:1637–1645 (1994).

Yates, III, Mass spectrometry and the age of the proteome, *J. Mass Spec.* 33:1–19 (1998).

Yen et al., Synthesis of water–soluble copolymers containing photocleavable bonds, *Makromol. Chem.* 190:69–82 (1989).

Zhang et al., Single–base mutational analysis of cancer and genetic diseases using membrane bound modified oligonucleotides, *Nucl. Acids Res.* 19:3929–3933 (1991).

Zimmermann et al., Automated preparation and purification of M13 templates for DNA sequencing, *Meth. Mol. Cell. Biol.* 1:29–34 (1989).

Zuckermann et al., Efficient methods for attachment of thiol specific probes to the 3'–ends of synthetic oligodeoxyribonucleotides, *Nucleic Acids Research*, 15:13, 5305–5321 (1987).

O'Donnell–Maloney et al., "The development of microfabricated arrays for DNA sequencing and analysis" *TIBTECH* 14:401–407 (1996).

BEADS BOUND TO A SOLID SUPPORT AND TO NUCLEIC ACIDS

RELATED APPLICATIONS

This application is a continuation-in-part of U.S. Ser. No. 08/746,036 now U.S. Pat. No. 5,900,481 filed Nov. 6, 1996, entitled "Bead Linkers for Immobilizing Nucleic Acids to Solid Supports", now U.S. Pat. No. 5,900,481, the teachings of which are incorporated herein by reference.

BACKGROUND OF THE INVENTION

In the fields of molecular biology and biochemistry, as well as in the diagnosis of diseases, nucleic acid hybridization has become a powerful tool for the detection, isolation, and analysis of specific oligonucleotide sequences. Typically, such hybridization assays utilize an oligodeoxynucleotide probe that has been immobilized on a solid support; as for example in the reverse dot blot procedure (Saiki, R. K., Walsh, P. S., Levenson, C. H., and Erlich, H. A. (1989) *Proc. Natl. Acad Sci. USA* 86, 6230). More recently, arrays of immobilized DNA probes attached to a solid surface have been developed for sequencing by hybridization (SBH) (Drmanac, R., Labat, I., Brukner, I., and Crkvenjakov, R. (1989) *Genomics,* 4, 114–128), (Strezoska, Z., Paunesku, T., Radosavljevic, D., Labat, I., Drmanac, R., and Crkvenjakov, R. (1991) *Proc. Natl. Acad. Sci. USA,* 88, 10089–10093). SBH uses an ordered array of immobilized oligodeoxynucleotides on a solid support. A sample of unknown DNA is applied to the array, and the hybridization pattern is observed and analyzed to produce many short bits of sequence information simultaneously. An enhanced version of SBH, termed positional SBH (PSBH), has been developed which uses duplex probes containing single-stranded 3'- or 5'-overhangs. (Broude, N. E., Sano, T., Smith, C. L., and Cantor, C. R. (1994) *Proc. Natl. Acad Sci. USA,* 91, 3072–3076). It is now possible to combine a PSBH capture approach with conventional Sanger sequencing to produce sequencing ladders detectable, for example by gel electrophoresis (Fu, D., Broude, N. E., Köster, H., Smith, C. L., and Cantor, C. R. (1995) *Proc. Natl. Acad Sci. USA,* 92, 10162–10166).

For the arrays utilized in these schemes, there are a number of criteria which must be met for successful performance. For example, the immobilized DNA must be stable and not desorb during hybridization, washing, or analysis. In addition, the density of the immobilized oligodeoxynucleotide must be sufficient for the ensuing analyses. However, there must be minimal non-specific binding of DNA to the surface. In addition, the immobilization process should not interfere with the ability of immobilized probes to hybridize. For the majority of applications, it is best for only one point of the DNA to be immobilized, ideally a terminus.

In recent years, a number of methods for the covalent immobilization of DNA to solid supports have been developed which attempt to meet all the criteria listed above. For example, appropriately modified DNA has been covalently attached to flat surfaces functionalized with amino acids, (Running, J. A., and Urdea, M. S. (1990) *Biotechniques,* 8, 276–277), (Newton, C. R., et al., (1993) *Nucl. Acids. Res.,* 21, 1155–1162.), (Nikiforov, T. T., and Rogers, Y. H. (1995) *Anal Biochem.,* 227, 201–209) carboxyl groups, (Zhang, Y., et al., (1991) *Nucl. Acids Res.,* 19, 3929–3933), epoxy groups (Lamture, J. B., et al., (1994) *Nucl. Acids Res.* 22, 2121–2125), (Eggers, M. D., et al., (1994) *BioTechniques,* 17, 516–524) or amino groups (Rasmussen, S. R., et al., (1991) *Anal. Biochem.,* 198, 138–142). Although many of these methods were quite successful for their respective applications, when used to link nucleic acids to two-dimensional (flat) supports, the density of the immobilized oligodeoxynucleotide is often insufficient for the ensuing analyses (Lamture, J. B., et al., (1994) *Nucl. Acids Res.* 22, 2121–2125, Eggers, M. D., et al., (1994) *BioTechniques,* 17, 516–524).

SUMMARY OF THE INVENTION

In one aspect, the invention features novel compositions comprised of at least one bead conjugated to a solid support and further conjugated to at least one nucleic acid. The bead can be comprised of any of a variety of materials and may be swellable or nonswellable. Preferably the bead is made of a material selected from the group consisting of: silica gel, glass, magnet, Wang resin (4—(hydroxymethyl) phenoxymethylcopoly(styrene—1% divinylbenzene(DVB) resin), metal, plastic, cellulose, dextran cross-linked with epichlorohydrin (e.g., Sephadex$^R$), and agarose (e.g., Sepharose$^R$). In a preferred embodiment, the bead is of a size in the range of about 1 to about 100 μm in diameter. In another preferred embodiment, the solid support is selected from the group consisting of: a bead, capillary, plate, membrane, wafer, comb, pin, a wafer with pits, an array of pits or nanoliter wells.

In another aspect, the invention features preferred conjugation means for making the novel compositions. In a preferred embodiment, a covalent amide bond is formed between the bead and the insoluble support. In a particularly preferred embodiment, the covalent amide bond is formed by reacting a carboxyl-functionalized bead with an amino-functionalized solid support; or a carboxyl-functionalized support with an amino-functionalized bead.

In a further aspect, the invention features methods for isolating target nucleic acids from a sample or reaction mixture by a conjugation means described herein. In a particularly preferred method, the nucleic acids are directly analyzed by mass spectrometry.

In a final aspect, the invention features kits containing reagents for performing the conjugations and thereby immobilizing nucleic acids to an insoluble support via a bead linker.

As compared to "flat" surfaces, beads linked to a solid support provide an increased surface area for immobilization of nucleic acids. Furthermore, by selecting a bead with the desired functionality, a practitioner can select a functionalization chemistry for immobilizing nucleic acids, which is different from the chemistry of the solid support.

The above and further features and advantages of the instant invention will become clearer from the following Detailed Description and claims.

BRIEF DESCRIPTION OF THE DRAWINGS

FIG. 9 depicts various pin conformations.

DETAILED DESCRIPTION OF THE INVENTION

In general, the invention relates to use of functionalized beads for the immobilization of nucleic acids, wherein the beads are stably associated with a solid support.

Figure 1:
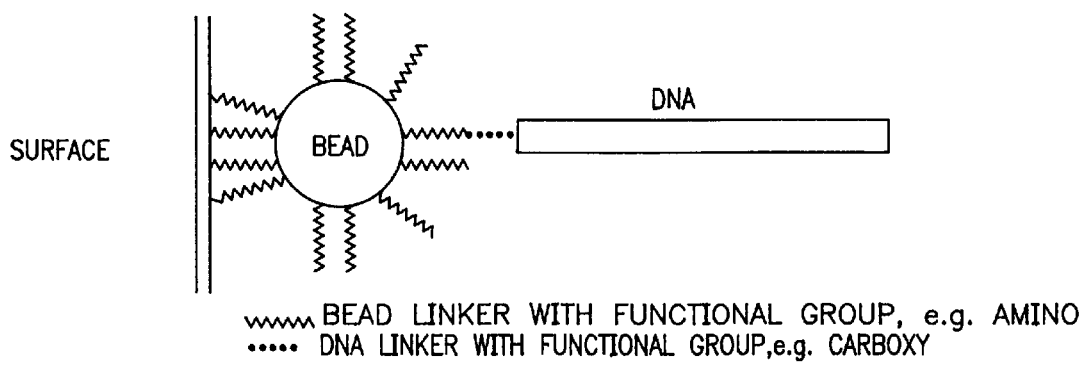
FIG. 1 is a schematic showing the covalent attachment of a bead to a solid support and DNA to the bead.
Figure 2:
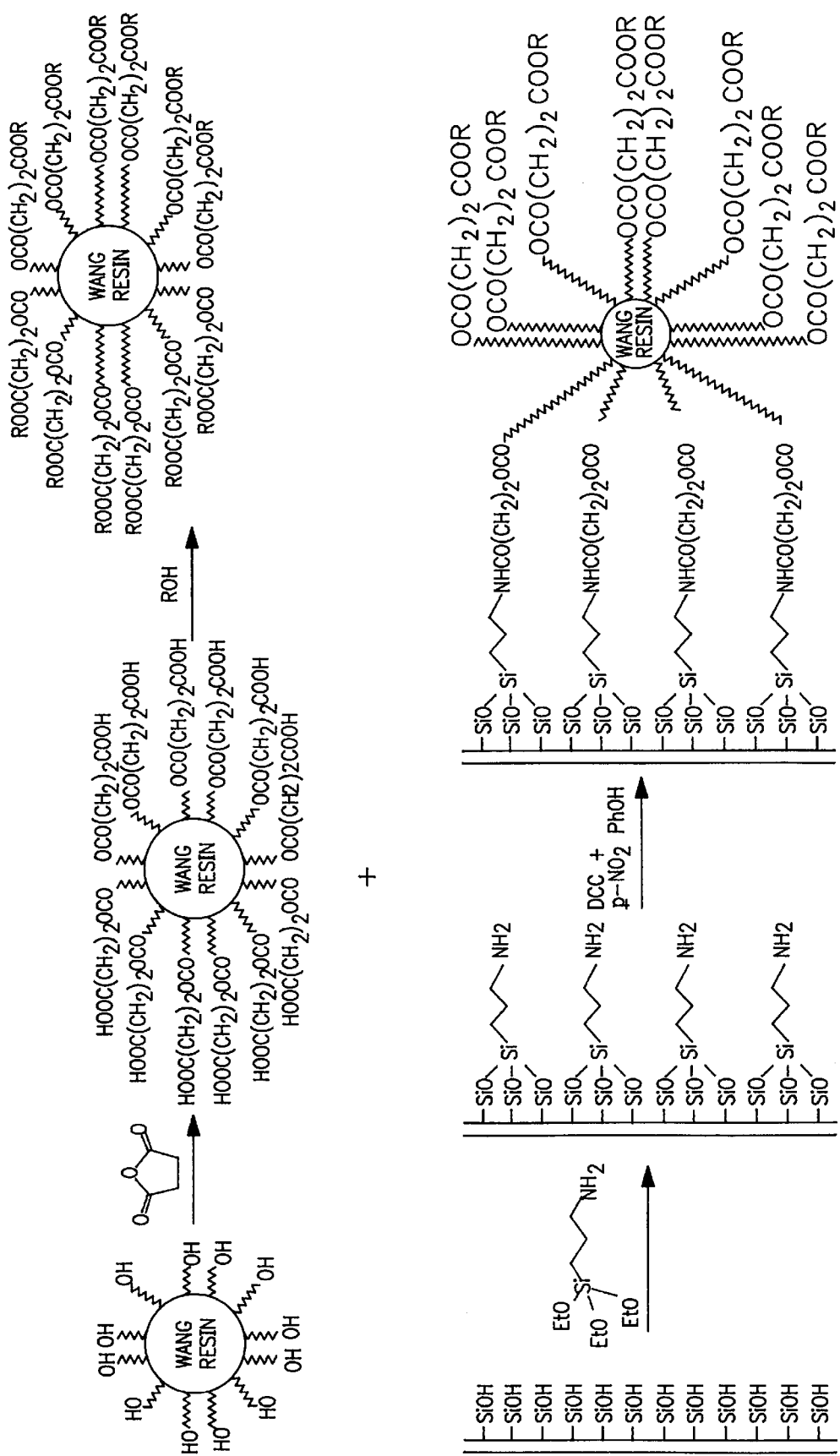
FIG. 2 is a schematic showing the covalent attachment of (4—(hydroxymethyl)phenoxymethylcopoly(styrene—1% divinylbenzene(DVB) resin) beads to a solid support as described in Example 1.
Figure 3:
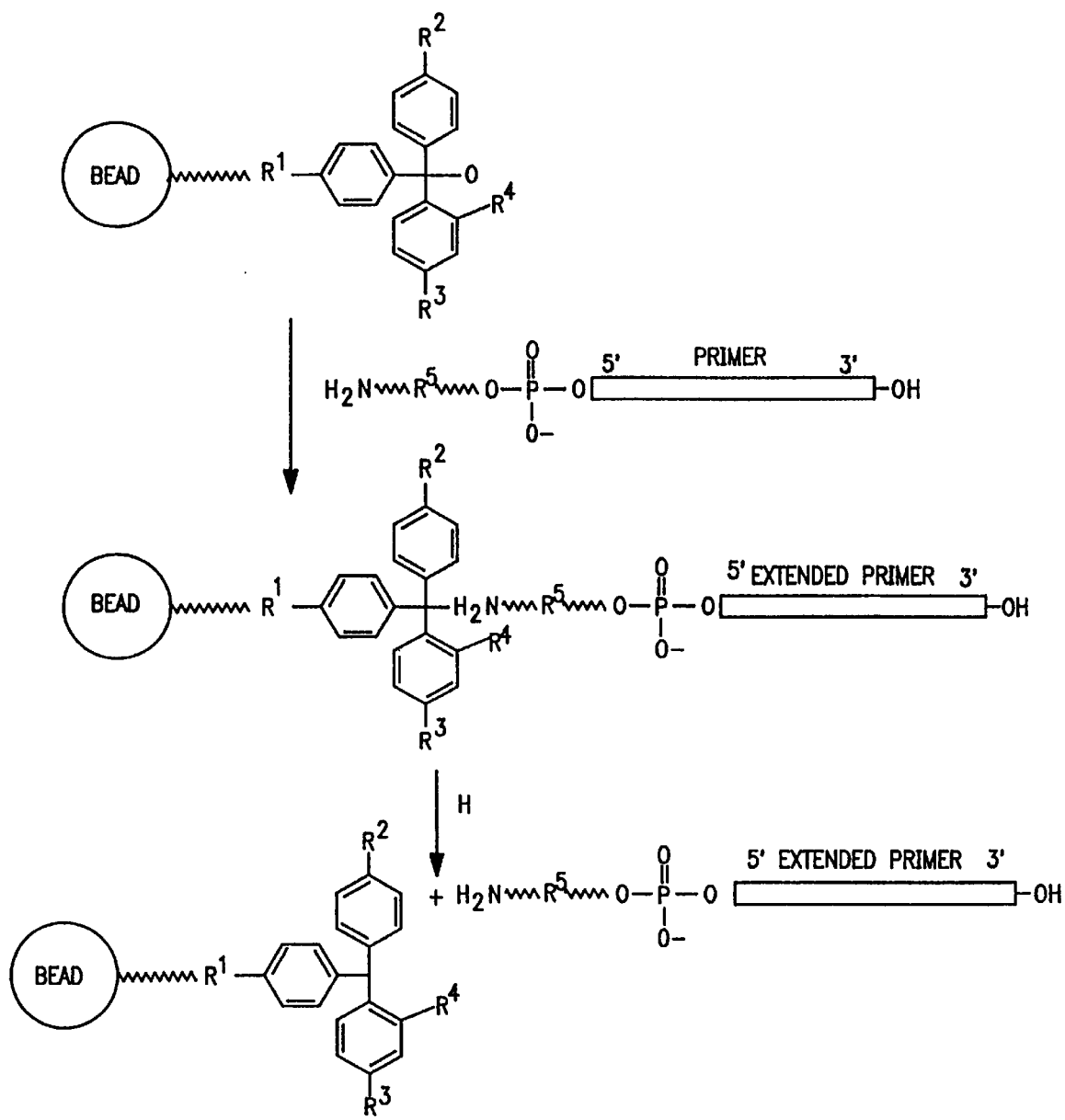
FIG. 3 is a schematic representation of nucleic acid immobilization via covalent bifunctional trityl linkers as described in Example 2.
Figure 4:
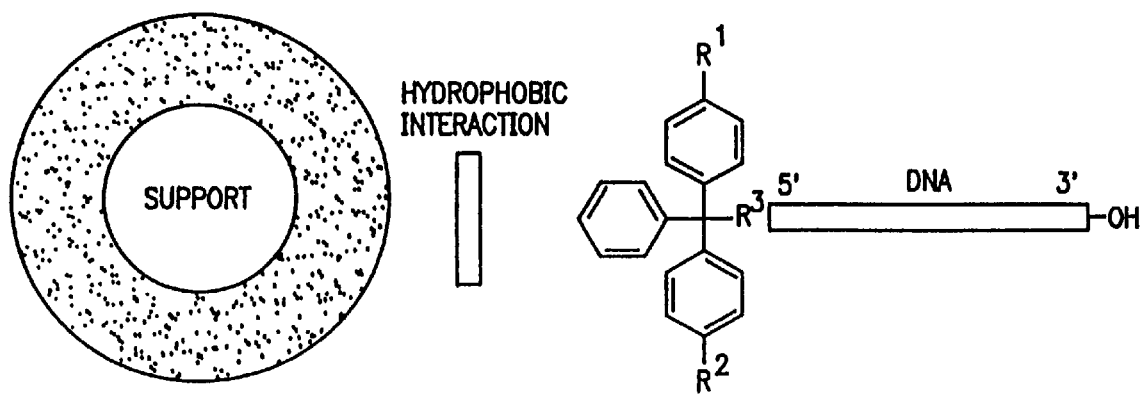
FIG. 4 is a schematic representation of nucleic acid immobilization via hydrophobic trityl linkers as described in Example 3.

FIG. 1 depicts a bead conjugated to a solid support through one or more covalent or non-covalent bonds. Nucleic acids can be immobilized on the functionalized bead before, during or after the bead is conjugated to the solid support. As used herein, the term "nucleic acid" refers to single stranded and/or double stranded polynucleotides such as deoxyribonucleic acid (DNA), and ribonucleic acid (RNA) as well as analogs or derivatives of either RNA or DNA. Also included in the term "nucleic acid" are analogs of nucleic acids such as peptide nucleic acid (PNA), phosphorothioate DNA, and the like.

Preferred nucleic acids for use in the subject invention are derivatized to contain at least one reactive moiety. Preferably the reactive moiety is at the 3' or 5' end. Alternatively, a nucleic acid can be synthesized with a modified base. In addition, modification of the sugar moiety of a nucleotide at positions other than the 3' and 5' position is possible through conventional methods. Also, nucleic acid bases can be modified, e.g., by using N7- or N9-deazapurine nucleosides or by modification of C-5 of dT with a linker arm, e.g., as described in F. Eckstein, ed., "Oligonucleotides and Analogues: A Practical Approach," IRL Press (1991). Alternatively, backbone-modified nucleic acids (e.g., phosphoroamidate DNA) can be used so that a reactive group can be attached to the nitrogen center provided by the modified phosphate backbone.

In preferred embodiments, modification of a nucleic acid, e.g., as described above, does not substantially impair the ability of the nucleic acid or nucleic acid sequence to hybridize to its complement. Thus, any modification should preferably avoid substantially modifying the functionalities of the nucleic acid which are responsible for Watson-Crick base pairing. The nucleic acid can be modified such that a non-terminal reactive group is present, and the nucleic acid, when immobilized to the support, is capable of self-complementary base pairing to form a "hairpin" structure having a duplex region.

Examples of insoluble supports for use in the instant invention include beads (silica gel, controlled pore glass, magnetic beads, biomagnetic separation beads such as Dynabeads$^R$, Wang resin; Merrifield resin, which is chloromethylated copolystyrene—divinylbenzene(DVB) resin, Sephadex$^R$/Sepharose$^R$ beads, cellulose beads, etc.), capillaries, flat supports such as glass fiber filters, glass surfaces, metal surfaces (steel, gold, silver, aluminum, silicon and copper), plastic materials including multiwell plates or membranes (e.g., of polyethylene, polypropylene, polyamide, polyvinylidenedifluoride), wafers, combs, pins or needles (e.g., arrays of pins suitable for combinatorial synthesis or analysis) or beads in an array of pits or nanoliter wells of flat surfaces such as wafers (e.g. silicon wafers), wafers with pits with or without filter bottoms.

An appropriate "bead" for use in the instant invention includes any three dimensional structure that can be conjugated to a solid support and provides an increased surface area for binding of DNA. Preferably the bead is of a size in the range of about 1 to about 100 μm in diameter. For use in the invention, a bead can be made of virtually any insoluble or solid material. For example, the bead can be comprised of silica gel, glass (e.g. controlled-pore glass (CPG)), nylon, Wang resin, Merrifield resin, Sephadex$^R$, Sepharose$^R$, cellulose, magnetic beads, Dynabeads$^R$, a metal surface (e.g. steel, gold, silver, aluminum, silicon and copper), a plastic material (e.g., polyethylene, polypropylene, polyamide, polyester, polyvinylidenedifluoride (PVDF)) and the like. Beads can be swellable, e.g., polymeric beads such as Wang resin, or non-swellable (e.g., CPG).

As used herein, the term "conjugated" refers to ionic or covalent attachment. Preferred conjugation means include: streptavidin- or avidin- to biotin interaction; hydrophobic interaction; magnetic interaction (e.g. using functionalized Dynabeads); polar interactions, such as "wetting" associations between two polar surfaces or between oligo/polyethylene glycol; formation of a covalent bond, such as an amide bond, disulfide bond, thioether bond, or via crosslinking agents; and via an acid-labile linker. In a preferred embodiment for conjugating nucleic acids to beads, the conjugating means introduces a variable spacer between the beads and the nucleic acids. In another preferred embodiment, the conjugation is photocleavable (e.g. streptavidin- or avidin- to biotin interaction can be cleaved by a laser, for example for mass spectrometry).

Appropriate cross-linking agents for use in the invention include a variety of agents that are capable of reacting with a functional group present on a surface of the bead, insoluble support and or nucleic acid and with a functional group present in the nucleic acid and/or bead, respectively. Reagents capable of such reactivity include homo- and hetero-bifunctional reagents, many of which are known in the art. Heterobifunctional reagents are preferred. A preferred bifunctional cross-linking agent is N-succinimidyl(4-iodoacetyl) aminobenzoate (SIAB). However, other crosslinking agents, including, without limitation, dimaleimide, dithio-bis-nitrobenzoic acid (DTNB), N-succinimidyl-S-acetyl-thioacetate (SATA), N-succinimidyl-3-(2-pyridyldithio) propionate (SPDP), succinimidyl 4-(N-maleimidomethyl)cyclohexane-1-carboxylate (SMCC) and 6-hydrazinonicotimide (HYNIC) may also be used in the novel process. In certain embodiments, the cross-linking agent can be selected to provide a selectively cleavable bond when the nucleic acid molecule is immobilized on the insoluble support. For example, a photolabile cross-linker such as 3-amino-(2-nitrophenyl)propionic acid (Brown et al. (1995) *Molecular Diversity* 4–12 and Rothschild et al (1996) *Nucleic Acids Res.* 24:351–66) can be employed to provide a means for cleaving the nucleic acid from. the beads or insoluble (e.g., solid) support, if desired. For further examples of cross-linking reagents, see, e.g., S. S. Wong, "Chemistry of Protein Conjugation and Cross-Linking," CRC Press (1991), and G. T. Hermanson, "Bioconjugate Techniques," Academic Press (1995).

In one preferred embodiment, a covalent amide bond is formed between a bead and a insoluble support by reacting a carboxyl-functionalized bead with an amino-functionalized solid support (e.g., as described in Example 1, below, by reacting a carboxyl-functionalized Wang resin with an amino-functionalized silicon surface). Alternatively, a carboxyl-functionalized support can be reacted with an amino-functionalized bead, which take advantage of an acid-cleavable bifunctional trityl protection scheme employed for nucleic acid attachment. The bifunctional trityl linker can also be attached to the 4-nitrophenyl active ester on a resin (e.g. Wang resin) via an amino group as well as from a carboxy group via an amino resin.

In the bifunctional trityl approach, the beads may require treatment with a volatile acid (e.g. formic acid, trifluoracetic acid, etc.) to ensure that the nucleic acid is cleaved and can be removed. In which case, the nucleic acid may be deposited as a beadless patch at the bottom of a well in the solid support or on the flat surface of the solid support. After addition of matrix solution, the nucleic acid can then be desorbed into the mass spectrometer, for example.

The hydrophobic trityl linkers can also be exploited as acid-labile linkers by using a volatile acid or an appropriate matrix solution (e.g. a matrix solution containing, for example, 3-hydroxypicolinic acid (3-HPA) to cleave the aminolink trityl group from the nucleic acid molecule). Also, the acid lability can be changed. For example, trityl, monomethoxy, dimethoxy- or trimethoxytrityl can be changed to the appropriate p-substituted and even more acid labile tritylamine derivatives of the nucleic acids (i.e. trityl ether and tritylamine bonds to the nucleic acid can be made). Therefore, the nucleic acid may be removed from the hydrophobic linker, for example, by disrupting the hydrophobic attraction or by cleaving tritylether or tritylamine bonds under acidic or the usual mass spectrometry conditions (e.g. wherein the matrix, such as 3-HPA acts as an acid)

As pointed out above, the bead can also be associated with the solid support by non-covalent interactions. For example, a magnetic bead (e.g., a bead capable of being magnetized, e.g., a ferromagnetic bead) can be attracted to a magnetic solid support, and can be released from the support by removal of the magnetic field. Alternatively, the bead can be provided with an ionic or hydrophobic moiety, which can associate with, respectively, an ionic or hydrophobic moiety of the solid support. Also, a bead can be provided with a member of a specific binding pair, and become immobilized to a solid support provided with a complementary binding moiety. For example, a bead coated with avidin or streptavidin can be bound to a surface coated with biotin or derivatives of biotin such as imino-biotin. It will be appreciated that the binding members can be reversed, e.g., a biotin-coated bead can bind to a streptavidin-coated solid support. Other specific binding pairs contemplated for use in the invention include hormone-receptor, enzyme-substrate, nucleic acid-complementary nucleic acid, antibody-antigen and the like.

Examples of preferred binding pairs or linker/interactions are shown in the following Table 1

TABLE 1

| LINKER/INTERACTION | EXAMPLES |
|---|---|
| streptavidin-biotin[a,c]/photolabile biotin[b] | biotinylated pin, avidin beads, photolabile biotin DNA |
| hydrophobic[a] | C18-coated pin, tritylated DNA |
| magnetic[a] | electromagnetic pin, steptavidin Dynabeads, biotin DNA |
| acid-labile linker[b] | glass pin, bifunctional trityl-linked DNA |
| amide bond(s)[c] | silicon wafer, Wang resin, amino-linked DNA |
| disulfide bond[a] | silicon wafer, beads are bound on the flat surface forming arrays or in arrays of nanoliter wells, thiol beads, thiolated DNA |
| photocleavable bond/linker | |
| thioether bond[c] | silicon wafer, beads are bound on the flat surface forming arrays or in arrays of nanoliter wells, thiolated DNA |

[a]These interactions are reversible.
[b]These non-reversible interactions are rapidly cleaved.
[c]Unless cleavable-linkers are incorporated at some point in the scheme, only the complement of the solid-bound DNA can be analysed in these schemes.

In a particularly preferred embodiment the bead is conjugated to the solid support and/or the nucleic acid is conjugated to the bead using an acid-labile bond. For example, use of a trityl linker, as further described in the following Examples 2 and 3, can provide a covalent or hydrophobic conjugation. Regardless of the nature of the conjugation, the trityl group is readily cleaved in acidic conditions.

A nucleic acid can be bound to a bead which is itself bound to a solid support, e.g., by any of the chemistries discussed above for the attachment of nucleic acids to solid supports, or attachment of beads to solid supports.

In certain embodiments, the invention contemplates the use of orthogonally-cleavable linkers for binding the bead to the solid support, and for binding the nucleic acid to the bead. Thus, a bead can be selectively cleaved from the surface without cleaving the nucleic acid from the bead, while the nucleic acid is cleaved from the bead at a later stage. For example, a disulfide linker (which can be cleaved, using, e.g., DTT) could be employed to bind the bead to the solid surface, and a bead-nucleic acid linker involving an acid-cleavable bifunctional trityl group could be used to immobilize a nucleic acid to the bead. Alternatively the linkage of the nucleic acid could be cleaved while the linkage of the bead to the support remains intact.

A bead can be bound to a solid support through a linking group which can be selected to have a length and a chemical nature such that high-density binding of beads to the solid support, and/or high-density binding of nucleic acid to the beads, is promoted. Such a linking group would have a "tree-like" structure in providing a multiplicity of functional groups per attachment site on the solid support such as polylysine, polyglutamic acid, pentaerythrole and tris-hydroxy-aminomethane.

In certain embodiments, beads can be cross-linked to other beads, e.g., by use of homobifunctional crosslinking reagents. Cross-linked beads can provide additional mechanical strength compared to non-crosslinked beads.

The methods and compositions described herein, can be used to isolate (purify) target nucleic acids from biological samples (reactions). For example, the compositions and methods can be used to isolate particular nucleic acids, which are generated by cloning (Sambrook et al., Molecular Cloning : A Laboratory Manual, Cold Spring Harbor Laboratory Press, 1989), polymerase chain reaction (PCR) (C. R. Newton and A. Graham, PCR, BIOS Publishers, 1994), ligase chain reaction (LCR) (Wiedmann, M., et. al., (1994) PCR Methods Appl. Vol. 3, Pp. 57–64; F. Barany Proc. Natl. Acad. Sci USA 88, 189–93 (1991), strand displacement amplification (SDA) (G. Terrance Walker et al., Nucleic Acids Res. 22, 2670–77 (1994)) European Patent Publication Number 0 684 315 entitled "Strand Displacement Amplification Using Thernophilic Enzymes") and variations such as RT-PCR (Higuchi, et al., Bio/Technology 11:1026–1030 (1993)), allele-specific amplification (ASA), cycle sequencing and transcription based processes.

Further, the methods and compositions can be used to isolate or transfer particular nucleic acids during the performance of a particular reaction. For example, a PCR reaction can be performed to 'master' mix without addition of the dideoxynucleotides (d/ddNTPs) or sequencing primers. Aliquots can then be isolated via a conjugation means described herein and transferred, for example to a sequencing plate, where d/ddNTPs and primers can then be added to perform a sequencing reaction. Alternatively, the PCR can be split between A, C, G, and T master mixes. Aliquots can then be transferred to a sequencing plate and sequencing primers added.

For example, 0.4–0.5 pmol of PCR product can be used in a cycle-sequencing reaction using standard conditions, allowing each PCR to be used for 10 sequencing reactions (10×A, C, G, and T). The sequencing reactions can be carried out in a volume of 10 $\mu$l containing 5–6 pmol of 5'-labeled sequencing primer in a standard 384 microwell plate allowing up to 96 sequencing reactions (3360 bases at 35 bases per reaction). Alternatively, a 192 microwell plate approximately 5×5 cm in a 12×16 format can be used. This format allows up to 48 sequencing reactions to be carried out per well, resulting in 1680 bases per plate (at 35 bases per reaction). The format of the sequencing plate will determine the dimensions of the transfer agent (e.g. pin-tool).

Figure 8:
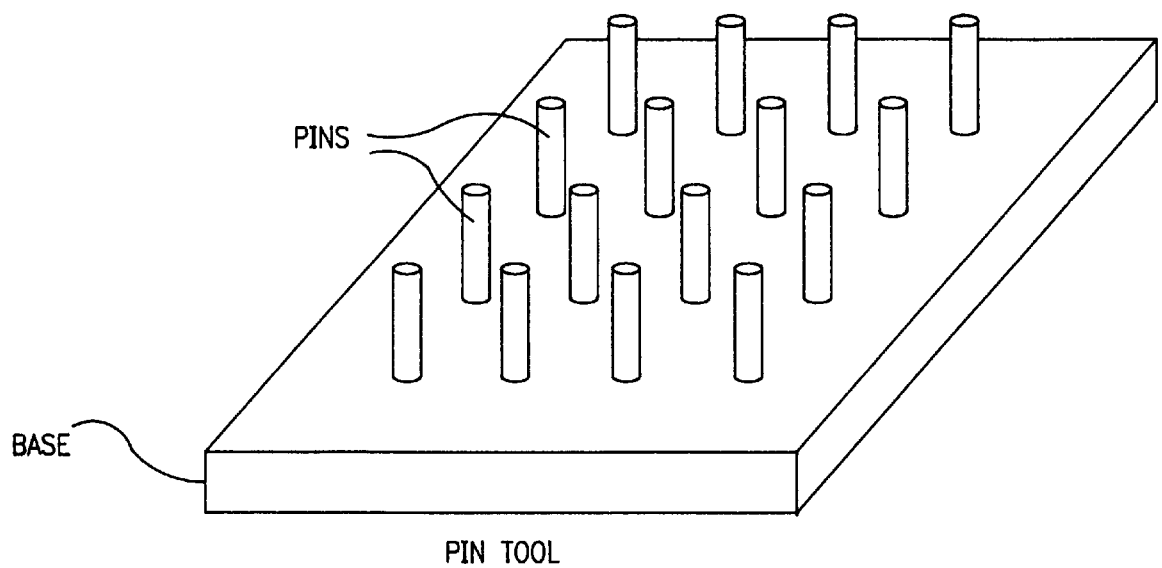
FIG. 8 schematically depicts a pin tool apparatus.
Figure 9A:
FIG. 9A shows a solid pin with a straight head.
Figure 9B:
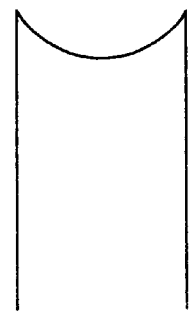
FIG. 9B shows a solid pin with a concave head.
Figure 9C:
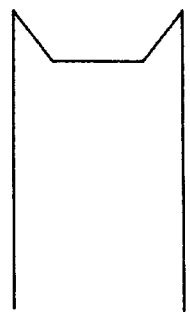
FIG. 9C shows a solid pin with a truncated pyramidal head.
Figure 9D:
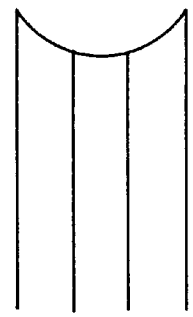
FIG. 9D shows a pin with a concave head and a hollowed center (through which can be inserted an optical fibre).
Figure 9E:
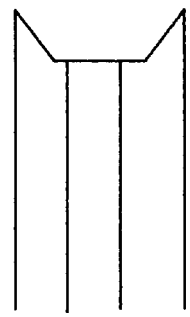
FIG. 9E shows a pin with a truncated pyramidal head and a hollowed center.
Figure 10:
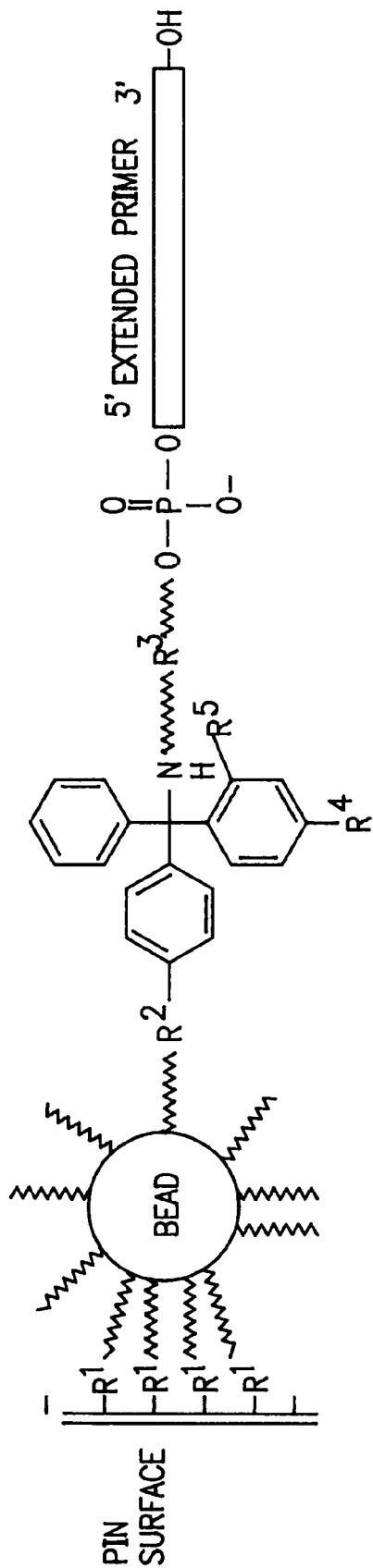
FIG. 10 is a schematic representation of the conjugation of beads (activated carboxyl) to pins (amino-functionalized) via amide bonds, and attachment of DNA (via an acid-cleavable linker) to beads. A disulfide linker conjugating the beads to the pins and a thioether conjugation between the bead and the trityl group permits selective cleavage of the beads (with DNA still attached) from the pin surface.
Figure 11:
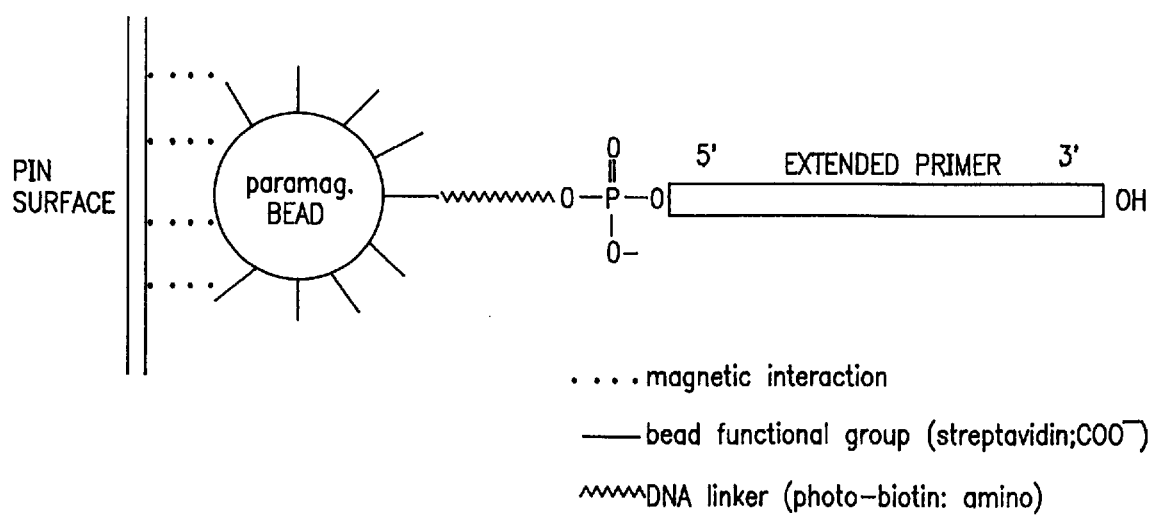
FIG. 11 is a schematic representation of paramagnetic beads functionalized with streptavidin to pins via a magnetic interaction and attachment of DNA (via a linker (e.g. modified biotin or photocleavable biotin) to allow selective cleavage of the DNA from the beads.

A pin tool in a 4×4 array (FIG. 8) can be applied to the wells of the sequencing plate and the sequencing products captured on functionalized beads as described herein, which are attached to the tips of the pins (>=1 pmol capacity). During the capture/incubation step, the pins can be kept in motion (vertical, 1–2 mm travel) to mix the sequencing reaction and increase the efficiency of the capture.

Figure 14:
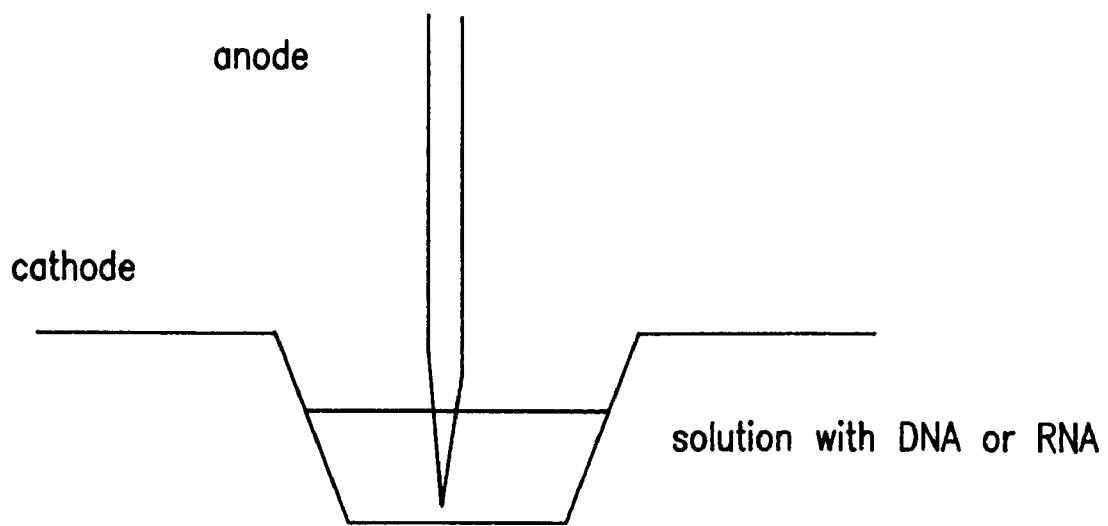
FIG. 14 schematically depicts a pintool onto which a voltage is applied. When an electrical field is applied, nucleic acids are attracted to the anode. This system purifies nucleic acids, since uncharged molecules would remain in solution, while positively charged molecules are attracted towards the cathode.

Alternatively, the nucleic acid can be directly captured onto the pin-tool, for example, a linking functionality on the pin-tool can immobilize the nucleic acid upon contact. Further, immobilization can result from application to the pin-tool of an electrical field, as shown in FIG. 14. When a voltage is applied to the pin-tool, the nucleic acids are attracted to the anode. This system also purifies nucleic acids, since uncharged molecules remain in solution and positively charged molecules are attracted to the cathode. For more specificity, the pin-tool (with or without voltage), can be modified to contain a partially or fully single stranded oligonucleotide (e.g. about 5–12 base pairs). Only complementary nucleic acid sequences (e.g. in solution) are then specifically conjugated to the pins.

In yet a further embodiment, a PCR primer can be conjugated to the tip of a pin-tool. PCR can be performed with the solid phase (pin-tool)-bound primer and a primer in solution, so that the PCR product becomes attached to the pin-tool. The pin-tool with the amplification product can then be removed from the reaction and analyzed (e.g. by mass spectrometry).

Examples of different pin conformations are shown in FIG. 9. For example, FIGS. 9a, 9b. and 9c. show a solid pin configuration. FIGS. 9d. and 9e show pins with a channel or hole through the center, for example to accomodate an optic fibre for mass spectrometer detection. The pin can have a flat tip or any of a number of configurations, including nanowell, concave, convex, truncated conic or truncated pyramidal (e.g. size 4–800$\mu$ across ×100$\mu$ depth). In a preferred embodiment, the individual pins are about 5 mm in length and about 1 mm in diameter. The pins and mounting plate can be made of polystyrene (e.g. one-piece injection moulded). Polystyrene is an ideal material to be functionalised and can be moulded with very high tolerances. The pins in a pin-tool apparatus may be collapsible (eg, controlled by a scissor-like mechanism), so that pins may be brought into closer proximity, reducing the overall size.

Captured nucleic acids can be analyzed by any of a variety of means including, for example, spectrometric techniques such as UV/VIS, IR, fluorescence, chemiluminescence, or NMR spectroscopy, mass spectrometry, or other methods known in the art, or combinations thereof. Preferred mass spectrometer formats include ionization (I) techniques, such as matrix assisted laser desorption (MALDI), continuous or pulsed electrospray (ESI) and related methods (e.g. Ionspray or Thermospray), or massive cluster impact (MCI); these ion sources can be matched with detection formats including linear or non-linear reflectron time-of-flight (TOF), single or multiple quadrupole, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed.

If conditions preclude direct analysis of captured DNA, then the DNA can be released and/or transferred. However, it may be important that the advantages of sample concentration are not lost at this stage. Ideally, the sample should be removed from the surface in as little a volume of eluent as possible, and without any loss of sample. Another alternative is to remove the beads (+sample) from the surface, where relevant, and measure the sample directly from the beads.

For example, for detection by mass spectrometry, the pin-tool can be withdrawn and washed several times, for example in ammonium citrate to condition the sample before addition of matrix. For example, the pins can simply be dipped into matrix solution. The concentration of matrix can then be adjusted such that matrix solution only adheres to the very tip of the pin. Alternatively, the pintool can be inverted and the matrix solution sprayed onto the tip of each pin by a microdrop device. Further, the products can be cleaved from the pins, for example into a nanowell on a chip, prior to addition of matrix.

Figure 12A:
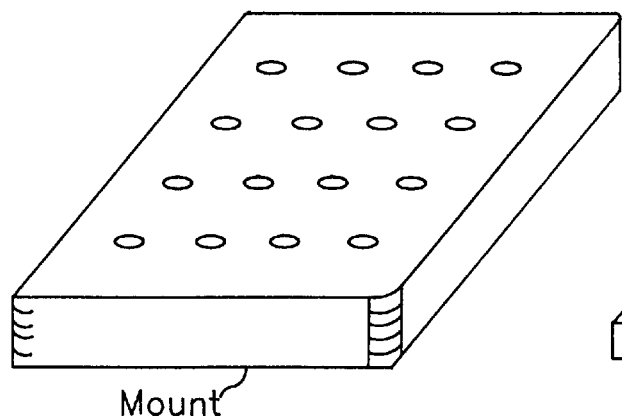
FIGS. 12 A–C schematically represent a pintool apparatus and mount, each separately and a cross section of the mount and tool installed.
Figure 12B:
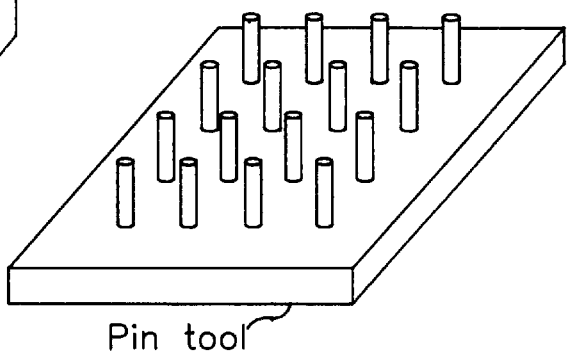
Figure 12C:
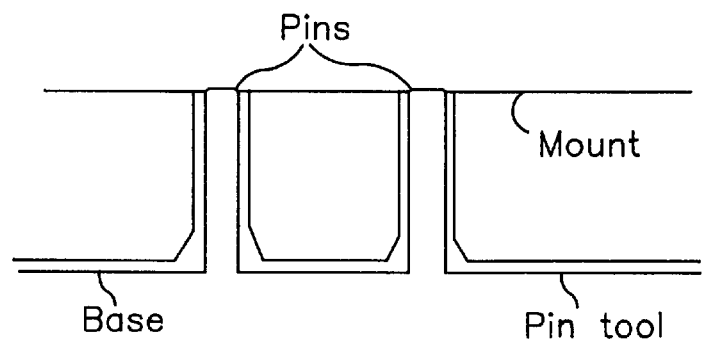

For analysis directly from the pins, a stainless steel 'mask' probe can be fitted over the pins in one scheme (FIG. 12) which can then be installed in the mass spectrometer.

Figure 13:
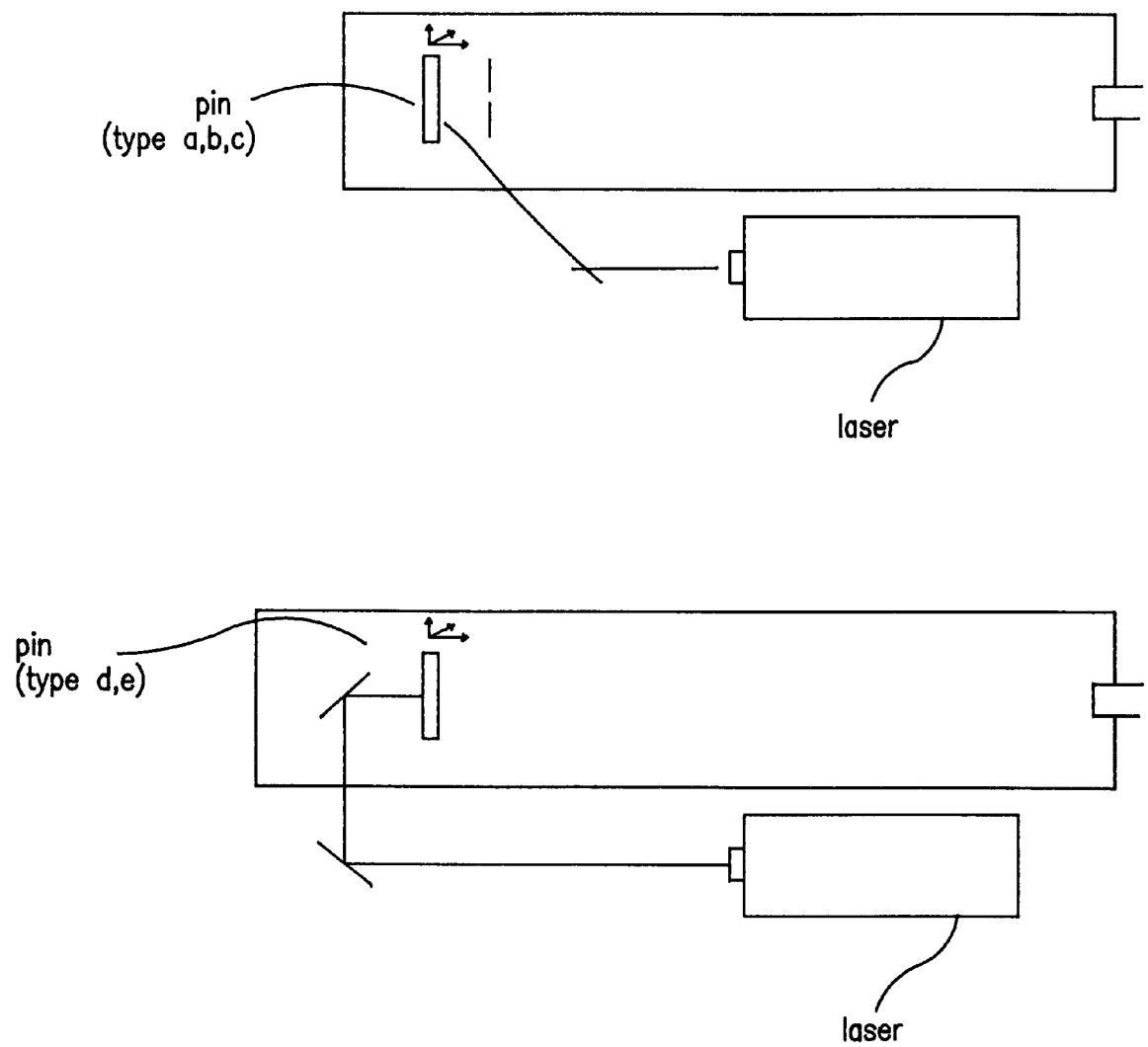
FIG. 13 is a schematic representation of mass spectrometry geometries for the pin conformations shown in FIGS. 9A–E.

Two mass spectrometer geometries for accomodating the pin-tool apparatus are proposed in FIG. 13. The first accomodates solid pins. In effect, the laser ablates a layer of material from the surface of the crystals, the resultant ions being accelerated and focused through the ion optics. The second geometry accomodates fibre optic pins in which the samples are lasered from behind. In effect, the laser is focused onto the pin-tool back plate and into a short optical fibre (about 100 $\mu$m in diameter and about 7 mm length to include thickness of the back plate). This geometry requires the volatilised sample to go through the depth of the matrix/bead mix, slowing and cooling down the ions resulting in a type of delayed extraction which should actually increase the resolution of the analysis.

The probe through which the pins are fitted can also be of various geometries. For example, a large probe with multiple holes, one for each pin, fitted over the pin-tool. The entire assembly is translated in the X-Y axes in the mass spectrometer. Alternatively, as a fixed probe with a single hole, which is large enough to give an adequate electric field, but small enough to fit between the pins. The pin-tool is then translated in all three axes with each pin being introduced through the hole for sequential analyses. This format is more suitable for the larger pin-tool (i.e. based on a standard 384 well microplate format). The two probes described above, are both suitable for the two mass spectrometer geometries described above.

Figure 15:
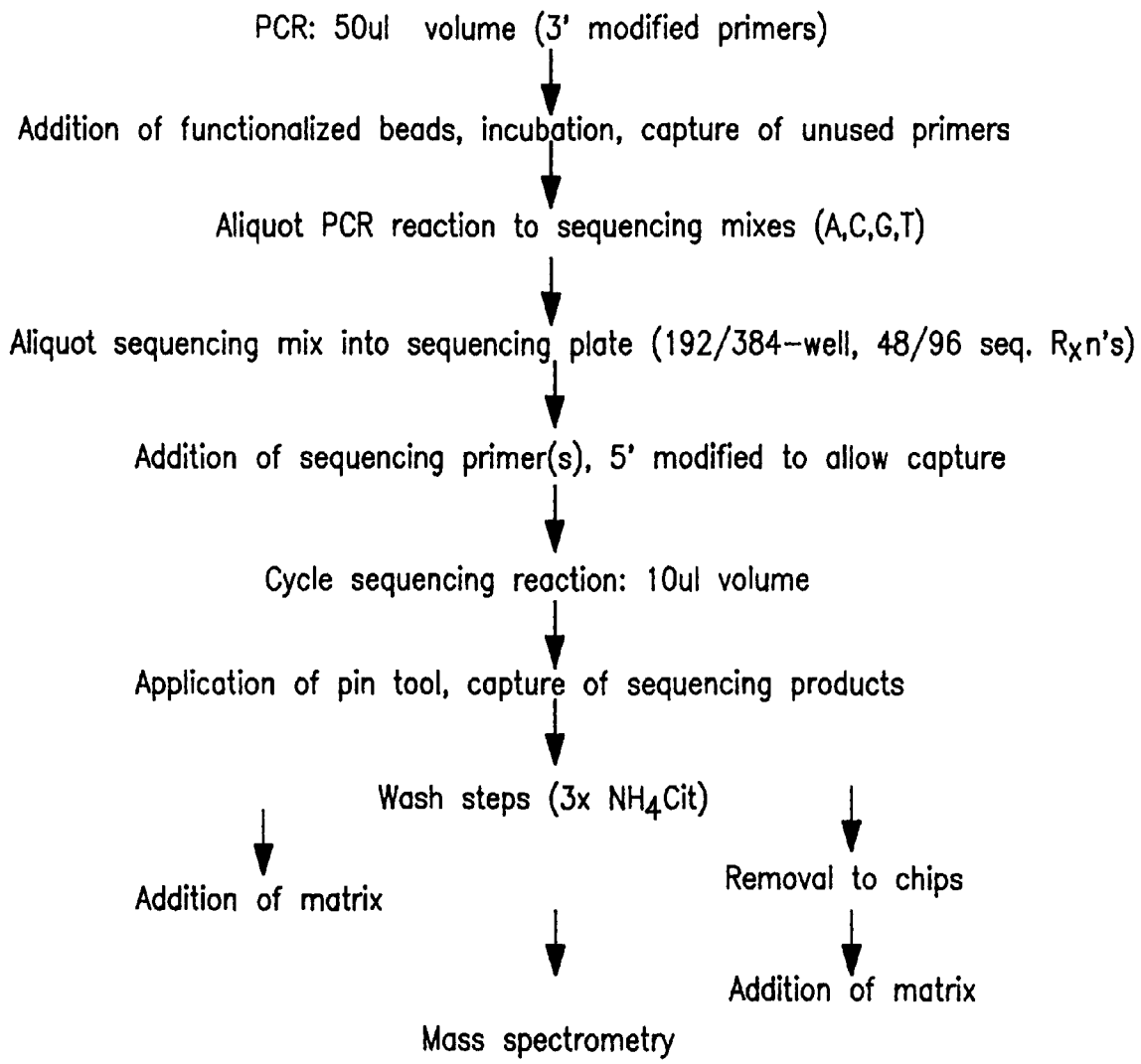
FIG. 15 shows a flow chart of the steps involved in sequencing by mass spectrometry using post-biology capture.

FIG. 15 schematically depicts the steps involved in mass spectrometry sequencing by post biology capture as described above.

The methods of the invention are useful for providing spatially-addressable arrays of nucleic acids immobilized on beads, which are further attached to solid supports. Such spatially addressable or pre-addressable arrays are useful in a variety of processes (e.g., SBH, quality control, and DNA sequencing diagnostics). In another aspect, the invention provides combinatorial libraries of immobilized nucleic acids bound to beads, which are further bound to a solid support as described above.

In still another aspect, the invention provides a kit for immobilizing nucleic acids on beads, which are further bound to a solid support. In one embodiment, the kit comprises an appropriate amount of: i) beads, and/or ii) the insoluble support, and iii) conjugation means. The kits described herein can also optionally include appropriate buffers; containers for holding the reagents; and/or instructions for use.

The present invention is further illustrated by the following Examples, which are intended merely to further illustrate and should not be construed as limiting. The entire contents of all of the references (including literature references, issued patents, published patent applications, and co-pending patent applications) cited throughout this application are hereby expressly incorporated by reference.

EXAMPLE 1

Attachment of Resin Beads to a Silicon Surface

A silicon surface (e.g. of a silicon wafer) is derivatized with amino groups by treatment with 3-aminopropyltriethoxysilane. Wang resin beads are treated with succinic anhydride to provide carboxyl-functionalized resin beads. The carboxyl-functionalized resin beads are then coupled to the amino-functionalized silicon surface with a coupling reagent (for example, dicyclohexylcarbodiimide (DCC)), in the presence of p-nitrophenol. The resin beads become covalently linked to the silicon surface, and the unreacted carboxyl groups of the resin are converted to the p-nitrophenyl ester (an activated ester suitable for coupling with a nucleic acid).

Alternatively, the carboxyl groups of the Wang resin are transformed to the p-nitrophenyl active esters prior to reacting with the amino-functionalized silicon surface.

Thus, resin beads can be rapidly and conveniently attached to a silicon surface, and can be simultaneously converted to a reactive form suitable for covalent attachment of nucleic acids.

EXAMPLE 2

Immobilization of Nucleic Acids on Solid Supports via an Scid-labile Covalent Bifunctional Trityl Linker Aminolink DNA was prepared and purified according to standard methods. A portion (10 eq) was evaporated to dryness on a speedvac and suspended in anhydrous DMF/pyridine (9:1; 0.1 ml). To this was added the chlorotrityl chloride resin (1 eq, 1.05 mol/mg loading) and the mixture was shaken for 24 hours. The loading was checked by taking a sample of the resin, detritylating this using 80% AcOH, and measuring the absorbance at 260nm. Loading was ca. 150 pmol/mg resin.

In 80% acetic acid, the half-life of cleavage was found to be substantially less than 5 minutes—this compares with trityl ether-based approaches of half-lives of 105 and 39 minutes for para and meta substituted bifunctional dimethoxytrityl linkers respectively. Preliminary results have also indicated that the 3-hydroxy picolinic acid matrix alone is sufficient to cleave the DNA from the chlorotrityl resin during MALDI mass spectrometry.

EXAMPLE 3

Immobilization of Nucleic Acids on Solid Supports via Hydrophobic Trityl Linker

The primer contained a 5'-dimethoxytrityl group attached using routine trityl-on DNA synthesis.

C18 beads from an oligo purification cartridge (0.2 mg) placed in a filter tip was washed with acetonitrile, then the solution of DNA (50 ng in 25 l) was flushed through. This was then washed with 5% acetonitrile in ammonium citrate buffer (70 mM, 250 l). To remove the DNA from the C18, the beads were washed with 40% acetonitrile in water (10 l) and concentrated to ca 2 l on the Speedvac or directly subjected to MALDI mass spectrometry.

Alternatively C18 beads were first covalently attached to a silicon surface (e.g. a silicon wafer) or adsorbed to a flat surface by hydrophobic interaction.

The results showed that acetonitrile/water at levels of ca.>30% are enough to dissociate the hydrophobic interaction. Since the matrix used in MALDI contains 50% acetonitrile, the DNA can be released from the support and MALDIed successfully (with the trityl group removed during the MALDI process).

EXAMPLE 4

Attaching Beads to Silicon Chips

Amino derivatisation of silicon surface

The silicon wafers were washed with ethanol to remove surface debris and flamed over a bunsen burner until "red hot" to ensure oxidation of the surface. After cooling, the wafers were immersed in an anhydrous solution of 3-aminopropyltriethoxysilane in toluene (25%v/v) for 3 hours. The wafers were then washed with toluene (three times) then anhydrous dimethylacetamide (three times).

Activation of Wang resin beads

Vacuum-dried Wang resin beads (5g, 0.84mmol/g loading, 4.2 mmol, diameter 100–200 mesh), obtained from Novabiochem, were suspended in pyridine (40 ml) with DMAP (0.1 eq, 0.42 mmol, 51 mg). To this was added succinic anhydride (5 eq, 21 mmol, 2.10 g) and the reaction was shaken for 12 hours at room temperature. After this time, the beads were washed with dimethylformamide (three times), then pyridine (three times) and suspended in pyridine/dimethylformamide (1:1, 20 ml). 4-Nitrophenol (2 eq, 8.4 mmol, 1.40 g) was added and the condensation was activated by adding dicyclohexylcarbodiimide (DCC) (2 eq, 8.4 mmol, 1.73 g) and the reaction mixture was shaken for 12 hours. The beads were then washed with dimethylformamide, pyridine and hexane, and stored at 4 C.

Coupling of Beads to Silicon Wafers

The amino-derivatised silicon wafer is treated with a suspension of the 4-nitrophenol beads in dimethyl acetamide (DMA), and within five minutes, the beads are covalently linked to the surface. The coated surface can then be washed with DMA, ethanol and water, under which conditions the beads remain as a uniform monolayer. Care must be taken to avoid scratching the beaded surface. The beads can then be reacted with the amino-functionalised modified DNA.

EXAMPLE 5

Immobilization of Nucleic Acids on Solid Supports via Streptavidin-Iminobiotin 2-iminobiotin N-hydroxy-succinimid ester (Sigma) was conjugated to the oligonucleotides with a 3'- or 5'-amino linker following the conditions suggested by the manufacture. The completion of the reaction was confirmed by MALDI-TOF MS analysis and the product was purified by reverse phase HPLC.

For each reaction, 0.1 mg of streptavidin-coated magnetic beads (Dynabeads M-280 Streptavidin from Dynal) were incubated with 80 pmol of the corresponding oligo in the presence of 1M NaCl and 50 mM ammonium carbonate (pH 9.5) at room temperature for one hour. The beads with bound oligonucleotides were washed twice with 50 mM ammonium carbonate (pH 9.5). Then the beads were incubated in 2 $\mu$l of 3-HPA matrix at room temperature for 2 min. An aliquot of 0.5 $\mu$l of supernatant was applied to MALDI-TOF. For biotin displacement experiment, 1.6 nmol of free biotin (80 fold excess to the bound oligo) in 1 $\mu$l of 50 mM ammonium citrate was added to the beads. After a 5 min. incubation at room temperature, 1 $\mu$l of 3-HPA matrix was added and 0.5 $\mu$l of supernatant was applied to MALDI-TOF MS. To maximize the recovery of the bound iminobiotin oligo, the beads from the above treatment were again incubated with 2 $\mu$l of 3-HPA matrix and 0.5 $\mu$l of the supernatant was applied to MALDI-TOF MS.

Figure 5:
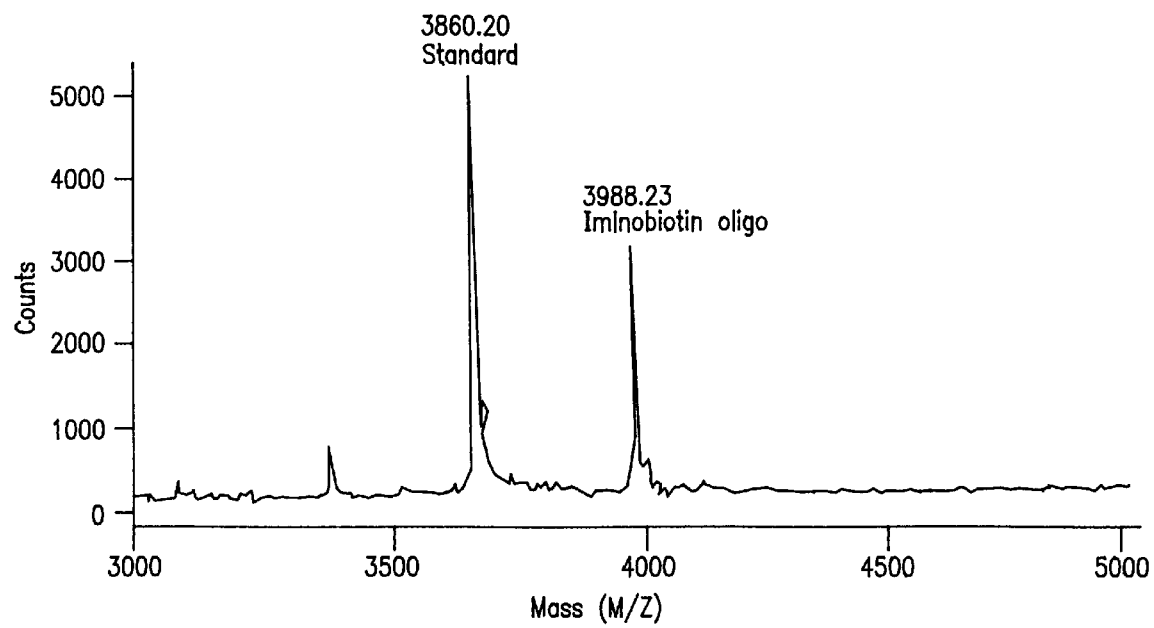
FIG. 5 shows a MALDI-TOF mass spectrum of a supernatant of the matrix treated Dynabeads containing bound oligo (5' iminobiotin-TGCACCTGACTC, SEQ. ID. No. 1). An internal standard (CTGTGGTCGTGC, SEQ. ID. No. 2) was included in the matrix.
Figure 6:
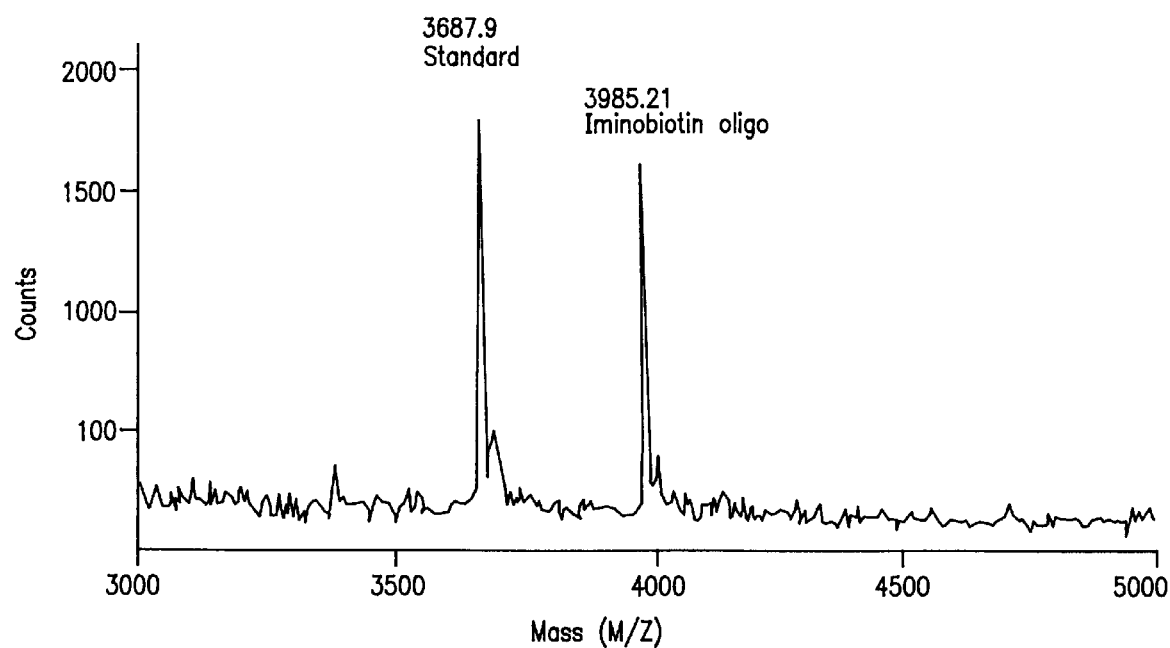
FIG. 6 shows a MALDI-TOF mass spectrum of a supernatant of biotin treated Dynabeads containing bound oligo (5' iminobiotin-TGCACCTGACTC, SEQ. ID. No. 1). An internal standard (CTGTGGTCGTGC, SEQ. ID. No. 2) was included in the matrix.
Figure 7:
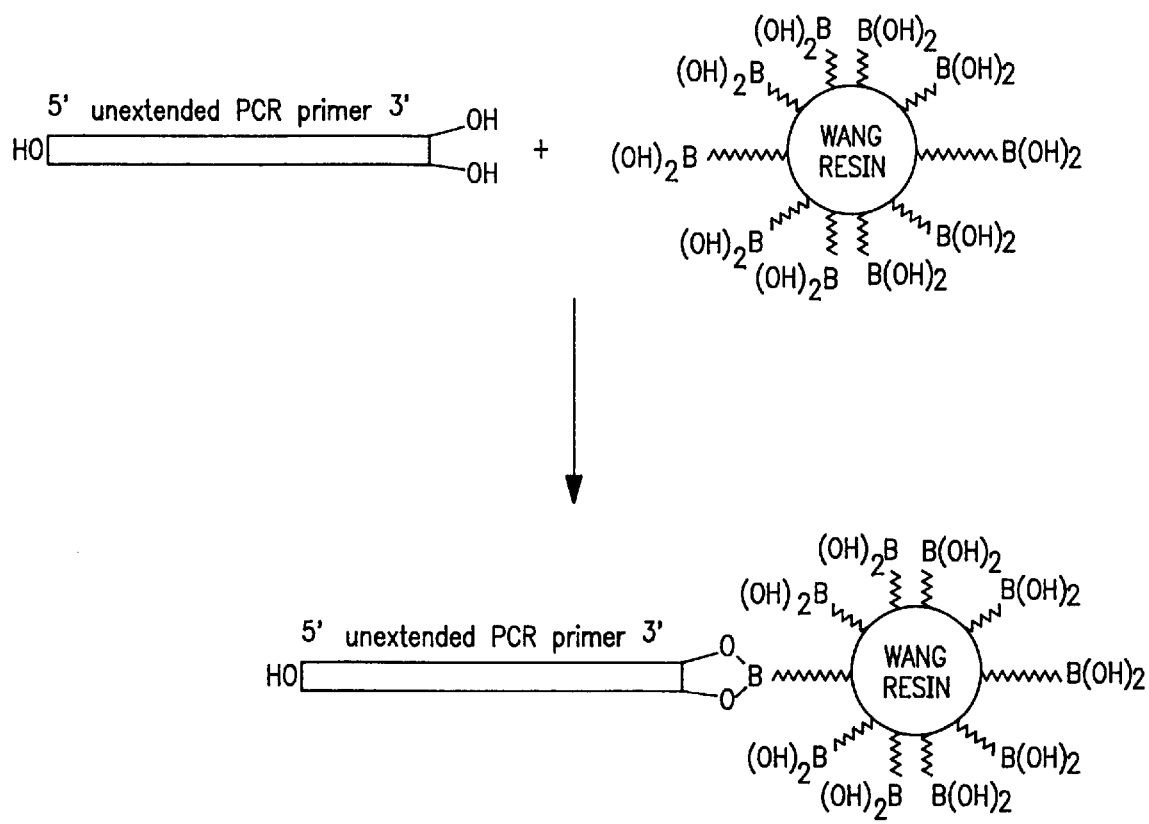
FIG. 7 schematically depicts conjugation of an unextended primer to a bead via reaction of a 2', 3'-diol on the primer with boronic acid functionalized beads.

Both matrix alone and free biotin treatment quantitatively released iminobiotin oligo off the streptavidin beads as shown in FIGS. 5 and 6. Almost no bound oligo was observed after the second treatment which confirmed the complete recovery Equivalents Those skilled in the art will recognize, or be able to ascertain using no more than routine experimentation, numerous equivalents to the specific procedures described herein. Such equivalents are considered to be within the scope of this invention and are covered by the following claims.

We claim:

1. A composition, comprising a bead conjugated to a solid support and further conjugated to a nucleic acid, wherein the solid support is selected from the group consisting of multiwell plates, arrays of pits and multiwell supports comprising nanoliter wells.

2. A composition of claim 1, wherein the bead is made from a material selected from the group consisting of: silica gel, glass, magnet, 4—(hydroxymethyl)phenoxymethylcopoly(styrene—1% divinylbenzene) resin, chloromethylated copolystyrene—divinylbenzene resin, metal, plastic, cellulose, dextran cross-linked with epichlorohydrin, and agarose.

3. A composition of claim 1, wherein the bead is swellable.

4. A composition of claim 1, wherein the bead is non-swellable.

5. A composition of claim 1, wherein the bead is in the range of 1 to 100 $\mu$m in diameter.

6. A composition of claim 1, wherein the nucleic acid is DNA.

7. A composition of claim 1, wherein the nucleic acid is RNA.

8. A process of making a bead conjugated to a solid support and further conjugated to a nucleic acid, comprising the steps of conjugating a bead to a nucleic acid; and conjugating a bead to a solid support, wherein the solid support is selected from the group consisting of multiwell plates, arrays of pits, and multiwell supports comprising nanoliter wells.

9. A process of claim 8, wherein the bead is functionalized.

10. A process of claim 9, wherein the bead is functionalized with carboxy functional groups.

11. A process of claim 9, wherein the bead is functionalized with amino functional groups.

12. A process of claim 9, wherein the bead is conjugated to the nucleic acid prior to conjugation of the bead to the solid support.

13. A process of claim 9, wherein the bead is conjugated to the nucleic acid after the bead is conjugated to the solid support.

14. A kit, comprising:
   i) beads,
   ii) an insoluble support, and
   iii) conjugation means for linking nucleic acids to the beads and the beads to the support.

15. The kit of claim 14, wherein the solid support is selected from the group consisting of: beads, capillaries, plates, membranes, wafers, combs, pins, wafers with arrays of pits, and supports with nanoliter wells.

16. The kit of claim 14, wherein the bead is made from material selected from the group consisting of silica gel, glass, magnet, p-benzyloxybenzyl alcohol copolystyrene-divinyl benzene (DVB) resin, chlorotritylchloride copolystyrene-DVB resin, chloromethylated copolystyrene-DVB resin, metal, plastic, cellulose, cross-linked dextran, and agarose gel.

17. A composition, comprising a bead conjugated to a solid support and further conjugated to a nucleic acid, wherein conjugation is effected with a crosslinking agent.

18. The method of claim 8, wherein conjugation is effected with a crosslinking agent.

19. A composition, comprising a bead conjugated to a solid support and further conjugated to a nucleic acid molecule comprising protein nucleic acid.

20. A composition, comprising a bead conjugated to a solid support and further conjugated to a nucleic acid, wherein conjugation is effected through a photocleavable linkage.

21. The composition of claim 20, wherein the linkage is cleaved by exposure to a laser.

22. The composition of claim 20, wherein the linkage is cleaved by exposure to electromagnetic radiation selected from ultravioltet, visible, infrared radiation or electromagnetic radiation generated by fluorescence or chemiluminescence, or combinations thereof.

23. A composition, comprising a bead conjugated to a solid support and further conjugated to a nucleic acid, wherein conjugation is effected through ionic linkages.

* * * * *

UNITED STATES PATENT AND TRADEMARK OFFICE
CERTIFICATE OF CORRECTION

PATENT NO. : 6,133,436
DATED : October 17, 2000
INVENTOR(S) : Koster et al.

It is certified that error appears in the above-identified patent and that said Letters Patent is hereby corrected as shown below:

IN THE SPECIFICATION:

at column 2, lines 58 and 59, replace "attachment of (4—(hydroxymethyl)phenoxymethylcopoly(styrene—1% divinylbenzene(DVB) resin) beads" with —attachment of Wang resin (4—(hydroxymethyl)phenoxymethylcopoly(styrene—1% divinylbenzene(DVB) resin) beads—;

at column 4, line 50, replace "Sephadex$^R$ , Sepharose$^R$ " with —Sephadex$^R$/Sepharose$^R$—;
at column 5, line 29, between "from" and "the" delete —.—;
at column 10, line 30, replace "Scid-labile" with —Acid-labile—;

Signed and Sealed this

Eighth Day of May, 2001

Attest:

NICHOLAS P. GODICI

*Attesting Officer*      *Acting Director of the United States Patent and Trademark Office*